(12) United States Patent
Saito et al.

(10) Patent No.: US 10,493,416 B2
(45) Date of Patent: Dec. 3, 2019

(54) THERMAL CONVECTION GENERATING CHIP AND LIQUID MEASURING DEVICE

(71) Applicant: OSAKA UNIVERSITY, Osaka (JP)

(72) Inventors: Masato Saito, Suita (JP); Yuichiro Kiriyama, Suita (JP); Eiichi Tamiya, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 15/308,645

(22) PCT Filed: May 8, 2015

(86) PCT No.: PCT/JP2015/063351
§ 371 (c)(1),
(2) Date: Nov. 3, 2016

(87) PCT Pub. No.: WO2015/170753
PCT Pub. Date: Nov. 12, 2015

(65) Prior Publication Data
US 2017/0189873 A1    Jul. 6, 2017

(30) Foreign Application Priority Data
May 8, 2014    (JP) .................. 2014-096990

(51) Int. Cl.
*B01L 3/00*    (2006.01)
*B01J 4/02*    (2006.01)
(Continued)

(52) U.S. Cl.
CPC .............. *B01J 4/02* (2013.01); *B01L 3/50273* (2013.01); *B01L 7/525* (2013.01); *C12M 1/00* (2013.01);
(Continued)

(58) Field of Classification Search
CPC ......... B01J 4/02; B01L 3/50273; B01L 7/525; C12M 1/00; G01N 21/07; G01N 37/00
(Continued)

(56) References Cited

U.S. PATENT DOCUMENTS 5,160,702 A * 11/1992 Kopf-Sill .......... B01L 3/502753
422/72
5,286,454 A *  2/1994 Nilsson ................. G01N 21/07
422/533
(Continued)

FOREIGN PATENT DOCUMENTS

JP    2005-114438 A     4/2005
JP    2007-315879 A    12/2007
(Continued)

OTHER PUBLICATIONS

International Search Report issued in PCT/JP2015/063351; dated Aug. 4, 2015.
(Continued)

Primary Examiner — Dean Kwak
(74) Attorney, Agent, or Firm — Studebaker & Brackett PC

(57) ABSTRACT

A thermal convection generating chip (1) includes a rotatory body (2), a thermal convection pathway (11) provided in the rotatory body (2), and a supply path (12A to 12C) that supplies a liquid to the thermal convection pathway (11). The supply path (12A to 12C) includes a liquid receiving section (121) that receives the liquid and a suction passage (122) that provides communication between the liquid receiving section (121) and the thermal convection pathway (11). The suction passage (122) has a first region (122*a*) extending between a midsection of the suction passage (122) and the thermal convection pathway (11), and a second region (122*b*) extending between the midsection and the liquid receiving section (121). The liquid in the first region (Continued)

(122a) is separated from the liquid in the second region (122b) through rotation of the rotatory body (2) to be supplied to the thermal convection pathway (11).

17 Claims, 16 Drawing Sheets

Specification includes a Sequence Listing.

(51) Int. Cl.
  *C12M 1/00* (2006.01)
  *G01N 37/00* (2006.01)
  *B01L 7/00* (2006.01)
  *G01N 21/07* (2006.01)
(52) U.S. Cl.
  CPC ...... *G01N 37/00* (2013.01); *B01L 2200/0605* (2013.01); *B01L 2200/142* (2013.01); *B01L 2300/0803* (2013.01); *B01L 2300/0867* (2013.01); *B01L 2300/0887* (2013.01); *B01L 2300/1805* (2013.01); *B01L 2400/0406* (2013.01); *B01L 2400/0409* (2013.01); *G01N 21/07* (2013.01)
(58) Field of Classification Search
  USPC .................. 422/415, 72, 501–504, 506, 507; 436/180
  See application file for complete search history.

(56) References Cited

U.S. PATENT DOCUMENTS

| | | | |
|---|---|---|---|
| 5,472,671 A | 12/1995 | Nilsson et al. | |
| 6,063,589 A | 5/2000 | Kellogg et al. | |
| 6,706,519 B1* | 3/2004 | Kellogg | B01F 13/0064 422/64 |
| 7,384,602 B2* | 6/2008 | Nagaoka | B01L 3/50273 422/50 |
| 7,695,685 B2* | 4/2010 | Koide | B01F 3/0807 422/502 |
| 9,939,439 B2* | 4/2018 | Viovy | G01N 33/56916 |
| 2003/0044322 A1* | 3/2003 | Andersson | B01F 5/0646 422/506 |
| 2004/0120856 A1* | 6/2004 | Andersson | B01J 19/0093 422/72 |
| 2004/0131345 A1* | 7/2004 | Kylberg | B01L 7/52 392/465 |
| 2006/0153735 A1* | 7/2006 | Nagaoka | G01N 21/07 422/547 |
| 2007/0003433 A1* | 1/2007 | Horike | B01L 3/502753 422/533 |
| 2008/0149190 A1* | 6/2008 | Bedingham | B01L 3/50273 137/340 |
| 2008/0152546 A1* | 6/2008 | Bedingham | B01L 3/502738 422/400 |
| 2009/0004059 A1 | 1/2009 | Pugia et al. | |
| 2009/0075801 A1* | 3/2009 | Hodko | B01L 3/50273 494/22 |
| 2009/0169430 A1 | 7/2009 | Yamamoto et al. | |
| 2009/0317896 A1* | 12/2009 | Yoo | B01L 3/502738 435/287.1 |
| 2011/0189701 A1* | 8/2011 | Kim | B01L 3/50273 435/7.9 |
| 2013/0109022 A1 | 5/2013 | Hwang | |
| 2015/0307927 A1* | 10/2015 | Nobile | B01L 3/50273 435/287.2 |
| 2016/0214112 A1 | 7/2016 | Saito et al. | |

FOREIGN PATENT DOCUMENTS

| | | | |
|---|---|---|---|
| JP | 2014-039498 | * | 3/2014 |
| JP | 2014-039498 A | | 3/2014 |
| JP | 2015-053881 A | | 3/2015 |
| WO | 90/13016 | | 11/1990 |
| WO | 1998/053311 A2 | | 11/1998 |
| WO | 2011/086497 A2 | | 7/2011 |
| WO | 2015/037255 A1 | | 3/2015 |

OTHER PUBLICATIONS

Masato Saito et al., "POCT o Shiko shita Enshin Sokusingata PCR Device no Kaihatsu to Oyo", Society for Chemistry and Micro-Nano Systems Kenkyukai Koen Yoshishu, Oct. 2, 2014 (Oct. 2, 2014), vol. 30th, p. 100, 3P09.

Yuichiro Kiriyama et al., "Micro Ryuro Enshin Device eno Bunshu Kino Fuyo no Kento", JSAP Autumn Meeting Koen Yokoshu (CD-ROM), Sep. 1, 2014 (Sep. 1, 2014), vol. 75th, Rombun No. 19P-A2-12.

Extended European Search Report (EESR) dated Nov. 27, 2017, from corresponding EP Appl No. 15788687.0, 13 pp.

* cited by examiner

```
SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
ggcaatatta ccgcacctca                                                   20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gtctgccact ttctccttgt                                                   20

<210> SEQ ID NO 3
<211> LENGTH: 30
<212> TYPE: DNA
<213> ORGANISM: Artificial Sequence
<220> FEATURE:
<223> OTHER INFORMATION: PCR primer

<400> SEQUENCE: 3
agatcttatg caaacttaat tggcaaatcc                                        30
```

THERMAL CONVECTION GENERATING CHIP AND LIQUID MEASURING DEVICE

TECHNICAL FIELD

The present invention relates to a thermal convection generating chip and a liquid measuring device.

BACKGROUND ART

Polymerase chain reaction (hereinafter, will be abbreviated as "PCR") is known as a gene amplification method. The PCR is a method that allows for amplification of a great amount of specific DNA fragments from an extremely small amount of DNA sample in a short time. The method is applied to a wide range of fields from clinical genetic diagnosis to food hygiene inspection and criminal investigation as well as basic research.

Thermal convection PCR has been offered as a facilitated PCR method. Patent Literature 1 discloses an example of a thermal convection PCR apparatus. The thermal convection PCR apparatus includes a cylindrical reaction vessel. The reaction vessel is angled relative to a vertical axis. A liquid mixture (a solution including a sample liquid and a reactant solution) is injected into the reaction vessel, and the liquid mixture is heated while the reaction vessel is being rotated about the vertical axis. Thus, thermal convection of the liquid mixture is generated.

CITATION LIST

Patent Literature

[Patent Literature 1]
WO 2011/086497

SUMMARY OF INVENTION

Technical Problem

However, the apparatus disclosed in Patent Literature 1 has the disadvantage that measuring out a liquid to be injected into the reaction vessel takes time and effort. That is, for injecting a liquid such as a sample liquid or a reactant solution into the reaction vessel, the liquid needs to be measured out accurately using a measuring device such as a micropipettor. However, such accurate measuring is difficult. Even a person of experience needs to spend great time and effort to perform such measuring.

In view of the above-described problem, the present invention has been made to provide a thermal convection generating chip and a liquid measuring device that can reduce time and effort to be spent by a user in order to measure out a liquid.

Solution to Problem

A thermal convection generating chip according to a first aspect of the present invention generates thermal convection of a liquid. The thermal convection generating chip includes a rotatory body, a thermal convection pathway provided in the rotatory body, and a supply path that supplies the liquid to the thermal convection pathway. The supply path includes: a liquid receiving section that receives the liquid; and a suction passage that provides communication between the liquid receiving section and the thermal convection pathway, and sucks the liquid in the liquid receiving section by capillary action. The suction passage has a first region and a second region. The first region extends between a midsection of the suction passage and the thermal convection pathway. The second region extends between the midsection and the liquid receiving section. The liquid in the first region is separated from the liquid in the second region through rotation of the rotatory body to be supplied to the thermal convection pathway.

In an embodiment, the suction passage bends at a sharp angle at the midsection.

In an embodiment, the suction passage further has an air inlet through which air is introduced into the midsection.

In an embodiment, the supply path supplies a sample liquid containing DNA or RNA to the thermal convection pathway.

In an embodiment, the supply path supplies a reactant solution for PCR or reverse transcription-PCR to the thermal convection pathway.

In an embodiment, the thermal convection generating chip includes a plurality of the supply paths, and the supply paths each supply a reactant solution for PCR or reverse transcription-PCR to the thermal convection pathway.

In an embodiment, the supply path supplies an evaporation inhibitor liquid to the thermal convection pathway. The evaporation inhibitor liquid inhibits evaporation of the liquid in the thermal convection pathway.

In an embodiment, the thermal convection generating chip includes a plurality of the supply paths. The supply paths include a supply path for supplying a sample liquid containing DNA or RNA to the thermal convection pathway and a supply path for supplying a reactant solution for PCR or reverse transcription-PCR to the thermal convection pathway. A total volume of a volume of the first region of the supply path for supplying the sample liquid to the thermal convection pathway and a volume of the first region of the supply path for supplying the reactant solution to the thermal convection pathway is equal to a volume of the thermal convection pathway.

In an embodiment, the thermal convection generating chip further includes an introduction chamber disposed between the first region of the suction passage and the thermal convection pathway, and a cover disposed on the rotatory body. The rotatory body has an opening. The introduction chamber is connected with one end portion of the first region and is in communication with a space outside the rotatory body through the opening. The cover covers the opening.

In an embodiment, the cover has a recess in communication with the space and with the introduction chamber. The recess has a first inner wall surface located opposite to the opening and a second inner wall surface intersecting with the first inner wall surface. An angle formed by the first inner wall surface and the second inner wall surface is an obtuse angle, or a boundary between the first inner wall surface and the second inner wall surface is a curved face having an arc-like cross-section.

In an embodiment, the supply path further includes a guide passage that guides the liquid in the liquid receiving section to the second region. The guide passage surrounds an entrance of the second region and has an open face located opposite to the entrance. The open face of the guide passage has an area larger than an aperture area of the entrance.

In an embodiment, the thermal convection generating chip includes a plurality of the thermal convection pathways.

In an embodiment, the thermal convection generating chip includes a plurality of the thermal convection pathways, and the supply path includes the liquid receiving section and a plurality of the suction passages. Each of the thermal convection pathways is provided with one of the suction passages between the thermal convection pathway and the liquid receiving section.

In an embodiment, the thermal convection generating chip includes a plurality of the supply paths. The supply paths cross over one another at different levels.

A liquid measuring device according to a second aspect of the present invention measures out a specified amount of liquid. The liquid measuring device includes a rotatory body, a liquid receiving section provided in the rotatory body, and a suction passage that is in communication with the liquid receiving section and sucks the liquid in the liquid receiving section by capillary action. The suction passage has a first region and a second region. The first region extends between a midsection of the suction passage and an end of the suction passage. The second region extends between the midsection and the liquid receiving section. The liquid in the first region is separated from the liquid in the second region through rotation of the rotatory body to be discharged from the end of the suction passage.

Advantageous Effects of Invention

The present invention can reduce time and effort to be spent by a user in order to measure out a liquid.

DESCRIPTION OF EMBODIMENTS

Figure 1:
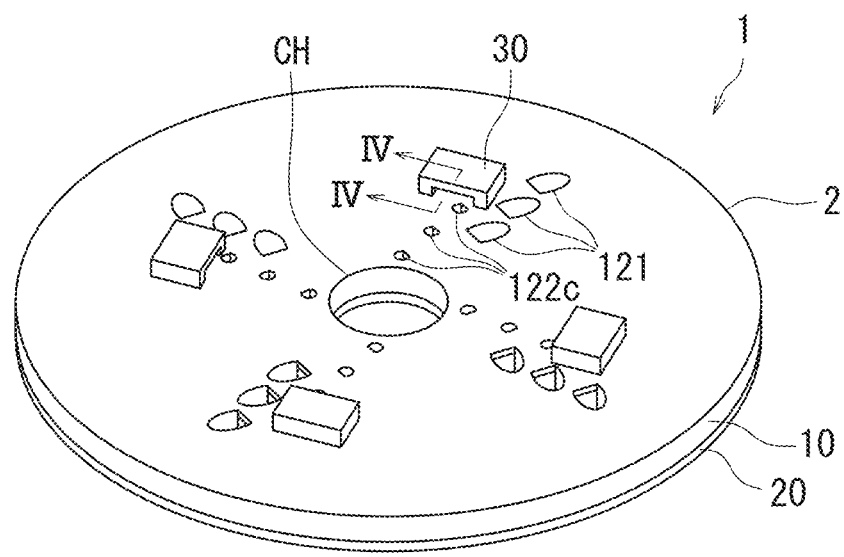
FIG. 1 is a perspective view of a thermal convection generating chip according to a first embodiment of the present invention.
Figure 2:
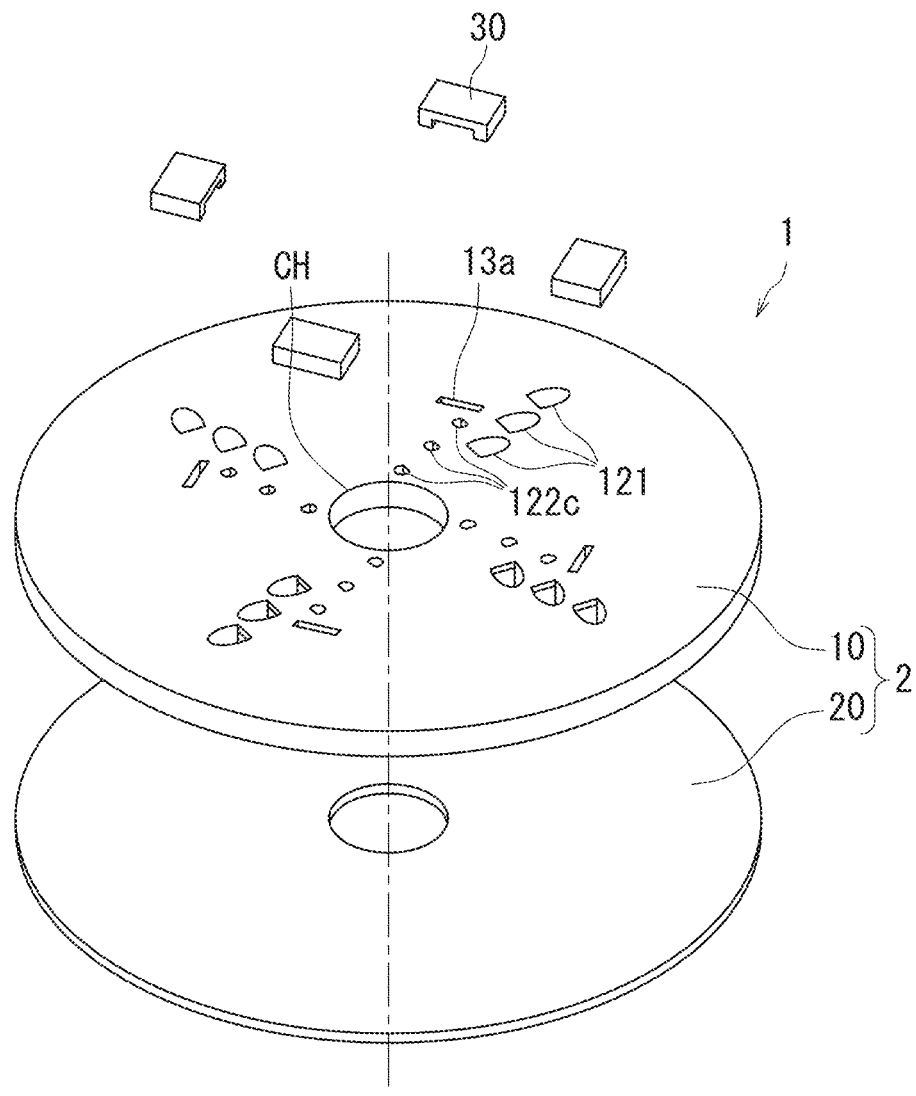
FIG. 2 is an exploded perspective view of the thermal convection generating chip illustrated in FIG. 1.
Figure 3A:
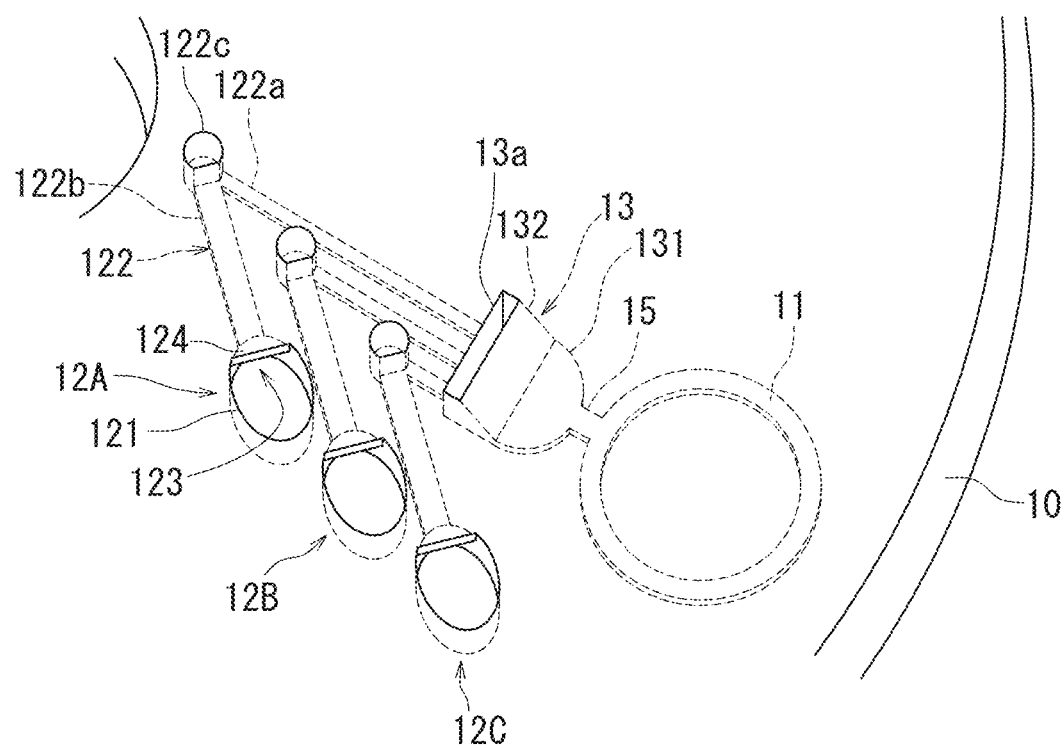
FIG. 3A is a partially enlarged, perspective view of a substrate of the thermal convection generating chip illustrated in FIG. 1.
Figure 3B:
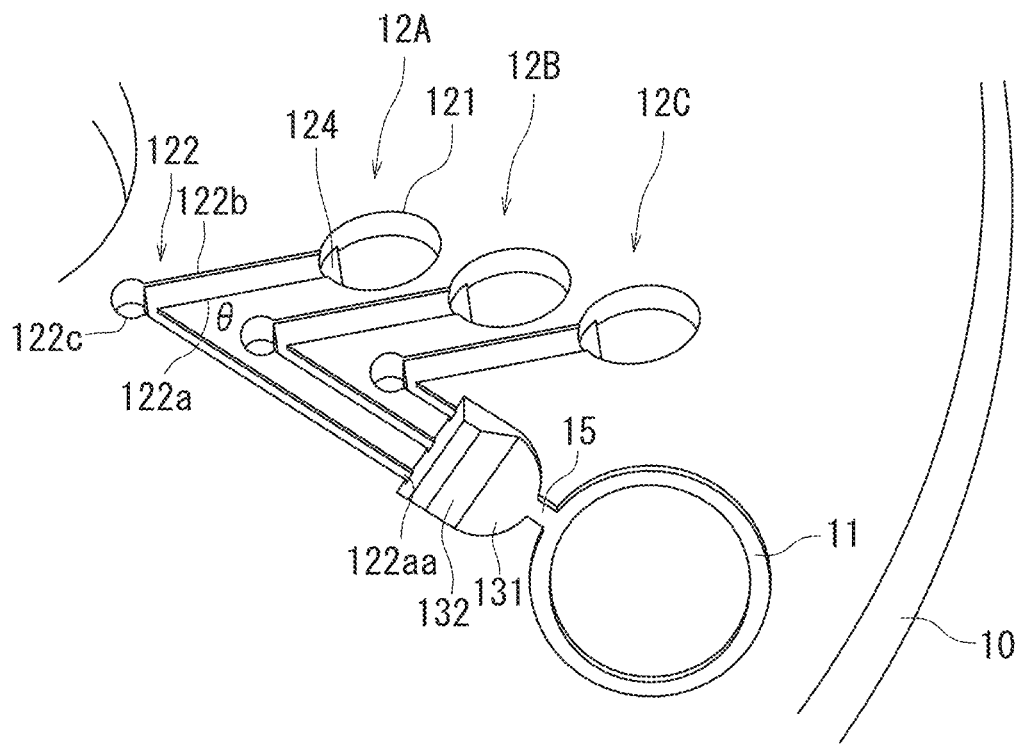
FIG. 3B is a partially enlarged, perspective view of the substrate of the thermal convection generating chip illustrated in FIG. 1.

The following describes embodiments of the present invention with reference to the accompanying drawings. FIG. 1 is a perspective view of a thermal convection generating chip 1 according to a first embodiment of the present invention. FIG. 2 is an exploded perspective view of the thermal convection generating chip 1. FIGS. 3A and 3B are each a partially enlarged, perspective view of a substrate 10 of the thermal convection generating chip 1. More specifically, FIG. 3A is a partially enlarged, perspective view of an upper surface side of the substrate 10, and FIG. 3B is a partially enlarged, perspective view of a lower surface side of the substrate 10.

As illustrated in FIG. 1, the thermal convection generating chip 1 includes a chip main body 2, which is a rotatory body. The chip main body 2 has a disk-like shape having a center hole CH at a center thereof. As illustrated in FIG. 2, the chip main body 2 includes the substrate 10 and a bottom plate 20 laminated to the substrate 10. As illustrated in FIGS. 3A and 3B, the substrate 10 includes a thermal convection pathway 11 and supply paths 12A to 12C.

Each of the supply paths 12A to 12C has a liquid receiving section 121 and a suction passage 122. The liquid receiving section 121 receives a liquid. The suction passage 122 provides communication between the liquid receiving section 121 and the thermal convection pathway 11, and sucks the liquid in the liquid receiving section 121 by capillary action.

The suction passage 122 has a first region 122a and a second region 122b. The first region 122a extends between a midsection of the suction passage 122 and the thermal convection pathway 11. The second region 122b extends between the midsection of the suction passage 122 and the liquid receiving section 121. The liquid in the first region 122a is separated from the liquid in the second region 122b through rotation of the chip main body 2 to be supplied to the thermal convection pathway 11.

The thermal convection pathway 11 is used to generate thermal convection of a liquid mixture of a sample liquid and a reactant solution (to be described later in detail). The thermal convection pathway 11 is a channel having an annular band-like shape in a plan view. The thermal convection pathway 11 includes a groove formed in a lower surface of the substrate 10. Dimensions of the thermal convection pathway 11 are not particularly limited. For example, the thermal convection pathway 11 has an outside diameter of 60 mm, a depth of 400 µm, and a width of 500 µm. According to the present embodiment, a plurality of the thermal convection pathways 11 are provided around a central axis of the substrate 10 at predetermined angular spacing.

The substrate 10 and the bottom plate 20 are for example formed from a synthetic resin. In particular, walls of the thermal convection pathways 11 are for example preferably formed from a cyclic olefin, a polypropylene, a polycarbonate, a complex of polydimethylsiloxane and glass, or an acrylic resin. Of the materials listed above, the cyclic olefin is most preferable, and the polypropylene or the polycarbonate is second most preferable in terms of their high degassing performance and heat resistance, and their low gas permeability, water absorption, and autofluorescence.

Each liquid receiving section 121 includes a hole. Each suction passage 122 bends at a sharp angle at the midsection thereof, in which the first region 122a extends in a radial direction of the substrate 10, and the second region 122b extends in a direction forming a sharp angle θ with the first region 122a. The first region 122a and the second region 122b each include a groove formed in the lower surface of the substrate 10. Through rotation of the chip main body 2, the liquid in the first region 122a is caused to move toward the thermal convection pathway 11 by centrifugal force, and the liquid in the second region 122b is caused to move toward the liquid receiving section 121 by centrifugal force. The angle θ is for example at least 5° and no greater than 85°.

Each suction passage 122 further has an air inlet 122c. Air is introduced into the midsection of the suction passage 122 through the air inlet 122c. The air inlet 122c includes a hole, providing communication between a space at the upper surface side of the substrate 10 and the first region 122a and the second region 122b. The air inlet 122c facilitates separation of the liquid in the first region 122a from the liquid in the second region 122b.

That is, when a gap formed between the liquid in the first region 122a and the liquid in the second region 122b is in vacuum, the liquid in the first region 122a and the liquid in the second region 122b are difficult to separate because each of the liquids is drawn toward the gap. The air hole 122c is provided thereby to introduce air into the gap, and thus the liquid in the first region 122a is separated from the liquid in the second region 122b smoothly. The air inlet 122c may be omitted so long as the liquid in the first region 122a can be separated from the liquid in the second region 122b smoothly without introducing air into the midsection of the suction passage 122.

The thermal convection generating chip 1 further includes introduction chambers 13 and introduction passages 15. Each introduction chamber 13 and each introduction passage 15 are provided between the corresponding thermal convection pathway 11 and the first regions 122a of the corresponding supply paths 12A to 12C. The liquid discharged from the first regions 122a of the supply paths 12A to 12C flow into the introduction chamber 13. The introduction chamber 13 will be described later in detail with reference to FIG. 4. The liquid in the introduction chamber 13 flows into the thermal convection pathway 11 through the introduction passage 15. The introduction passage 15 includes a groove formed in the lower surface of the substrate 10.

The supply path 12A supplies a sample liquid to the thermal convection pathway 11. The sample liquid is a liquid containing DNA or RNA. Examples of sample liquids include influenza viruses, norovirus, other general infectious disease viruses or bacteria, or extraction liquids from expressed RNA from cells. In the case of an influenza virus, a sample liquid is for example a suspension of a nasal secretion in a solution such as buffer solution or water. In the case of norovirus, a sample liquid is for example a suspension of vomit in a solution such as buffer solution or water.

The first region 122a of the supply path 12A for example has a depth of at least 10 µm and no greater than 1 mm. The first region 122a of the supply path 12A for example has a width of at least 10 µm and no greater than 1 mm. The first region 122a of the supply path 12A for example has a length of at least 1 mm and no greater than 30 mm. The second region 122b of the supply path 12A for example has a depth of at least 10 µm and no greater than 1 mm. The second region 122b of the supply path 12A for example has a width of at least 10 µm and no greater than 1 mm. The second region 122b of the supply path 12A for example has a length of at least 1 mm and no greater than 30 mm.

The amount of the sample liquid that fills the first region 122a of the supply path 12A is equal to the amount of the sample liquid that should be supplied to the thermal convection pathway 11. The liquid receiving section 121 of the supply path 12A has a greater volume than the suction passage 122 of the supply path 12A.

The supply path 12B supplies, to the thermal convection pathway 11, a reactant solution that is used for performing PCR or reverse transcription-PCR. Examples of reactant solutions include Platinum Quantitative RT-PCR ThermoScript One-Step System, SuperScriptIII OneStep RT-PCR System, and GeneAmp EZ rTth RNA PCR Kit, all of which are product names, produced by Life Technologies Japan Ltd.; PrimeScriptII High Fidelity One Step RT-PCR Kit, Primescript High Fidelity RT-PCR Kit, and SpeedSTAR HS DNA Polymerase, all of which are product names, produced by TAKARA BIO INC.; and Ampdirect, which is a product name, produced by Shimadzu Corporation.

The first region 122a of the supply path 12B for example has a depth of at least 10 µm and no greater than 1 mm. The first region 122a of the supply path 12B for example has a width of at least 10 µm and no greater than 1 mm. The first region 122a of the supply path 12B for example has a length of at least 1 mm and no greater than 30 mm. The second region 122b of the supply path 12B for example has a depth of at least 10 µm and no greater than 1 mm. The second region 122b of the supply path 12B for example has a width of at least 10 µm and no greater than 1 mm. The second region 122b of the supply path 12B for example has a length of at least 1 mm and no greater than 30 mm.

The amount of the reactant solution that fills the first region 122a of the supply path 12B is equal to the amount of the reactant solution that should be supplied to the thermal convection pathway 11. The liquid receiving section 121 of the supply path 12B has a greater volume than the suction passage 122 of the supply path 12B. A total volume of a volume of the first region 122a of the supply path 12A and a volume of the first region 122a of the supply path 12B is equal to a volume of the thermal convection pathway 11.

The supply path 12C supplies an evaporation inhibitor liquid to the thermal convection pathway 11. The evaporation inhibitor liquid is a liquid that inhibits evaporation of the liquids (the sample liquid and the reactant solution) in the thermal convection pathway 11, and examples thereof include mineral oil.

The mineral oil has a boiling point higher than a maximum temperature of a heater (not illustrated) for heating the sample liquid and the reactant solution in the thermal convection pathway 11, and therefore inhibits evaporation of the sample liquid and the reactant solution. The mineral oil has a lower specific gravity than the sample liquid and than the reactant solution, and therefore functions as a lid that blocks the introduction passage 15. A liquid other than mineral oil may be used as the evaporation inhibitor liquid so long as the liquid has either or both of a boiling point higher than the maximum temperature of the heater and a specific gravity smaller than the specific gravity of the sample liquid and than the reactant solution.

Through rotation of the thermal convection generating chip 1, the thermal convection pathway 11 is filled with the sample liquid and the reactant solution that each have a greater specific gravity than the mineral oil, and the mineral oil stays in the introduction passage 15 to block the introduction passage 15. As a result, evaporation of the sample liquid and the reactant solution in the thermal convection pathway 11, and back flow thereof into the introduction chamber 13 can be restricted.

The first region 122a of the supply path 12C for example has a depth of at least 10 μm and no greater than 1 mm. The first region 122a of the supply path 12C for example has a width of at least 10 μm and no greater than 1 mm. The first region 122a of the supply path 12C for example has a length of at least 1 mm and no greater than 30 mm. The second region 122b of the supply path 12C for example has a depth of at least 10 μm and no greater than 1 mm. The second region 122b of the supply path 12C for example has a width of at least 10 μm and no greater than 1 mm. The second region 122b of the supply path 12C for example has a length of at least 1 mm and no greater than 30 mm. A position and dimensions of each of the supply path 12A, the supply path 12B, and the supply path 12C are determined such that the supply path 12A, the supply path 12B, and the supply path 12C do not interfere with one another.

The amount of the mineral oil that fills the first region 122a of the supply path 12C is an amount sufficient to block the introduction passage 15. The liquid receiving section 121 of the supply path 12C has a greater volume than the suction passage 122 of the supply path 12C.

The thermal convection generating chip 1 further includes covers 30 (see FIG. 1). Openings 13a of the introduction chambers 13 are formed in the upper surface of the chip main body 2. The covers 30 are disposed on the chip main body 2 and cover the respective openings 13a. The introduction chambers 13 and the covers 30 will be described later in detail with reference to FIGS. 4 and 5.

Each of the supply paths 12A to 12C further includes a guide passage 123. Specifically, a portion of a top face of each liquid receiving section 121 is covered by a half-moon-shaped plate-like guide passage forming section 124, forming the guide passage 123 between the guide passage forming section 124 and the liquid receiving section 121. The guide passage 123 guides a liquid in the liquid receiving section 121 to the corresponding second region 122b. The guide passages 123 will be described later in detail with reference to FIG. 6.

Figure 4:
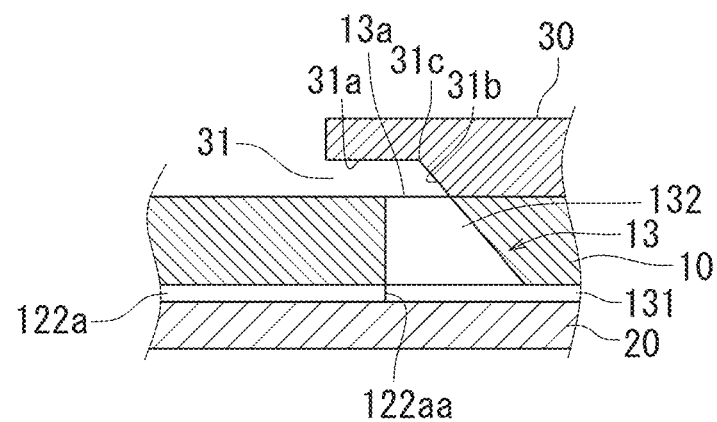
FIG. 4 is a cross-sectional view of the thermal convection generating chip taken along line IV-IV in FIG. 1.
Figure 5:
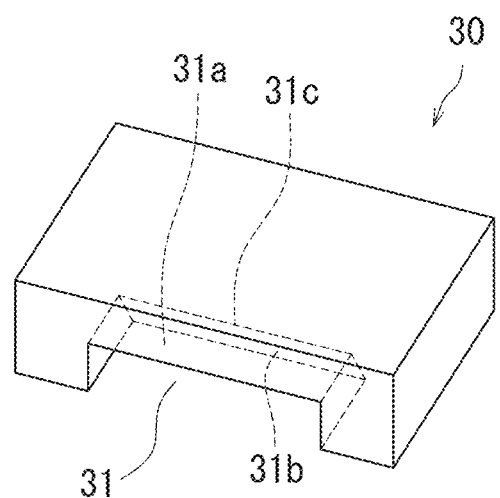
FIG. 5 is an enlarged perspective view of a cover of the thermal convection generating chip illustrated in FIG. 1.

Configurations of the introduction chambers 13 and the covers 30 will be described in detail with reference to FIGS. 4 and 5. FIG. 4 is a cross-sectional view taken along line IV-IV in FIG. 1. FIG. 5 is a perspective view of one cover 30.

As illustrated in FIG. 4, the substrate 10 is provided with grooves 131 and holes 132. Each introduction chamber 13 is formed from one groove 131 and one hole 132. Each groove 131 has a semi-oval shape in a plan view and is formed in the lower surface of the substrate 10. Each hole 132 has a trapezoidal vertical cross-section and is located above the corresponding groove 131. The hole 132 and the groove 131 are in communication with one another.

Each introduction chamber 13 is connected with one end portion 122aa of each of the first regions 122a of the corresponding supply paths 12A to 12C and is in communication with a space outside the chip main body 2 through the corresponding opening 13a. Furthermore, each introduction chamber 13 is in communication with the corresponding thermal convection pathway 11 through the corresponding introduction passage 15 (FIGS. 3A and 3B).

As illustrated in FIG. 5, each cover 30 is a member substantially in the shape of a rectangular parallelepiped and is formed from a synthetic resin or the like. Each cover 30 has a recess 31, and the recess 31 is in communication with the space outside the chip main body 2 and with the corresponding introduction chamber 13.

The recess 31 has a first inner wall surface 31a, a second inner wall surface 31b, and a boundary 31c. The inner wall surface 31a is located opposite to the opening 13a of the corresponding introduction chamber 13. The second inner wall surface 31b intersects with the first inner wall surface 31a and is at an angle relative to the first inner wall surface 31a. The angle formed by the first inner wall surface 31a and the second inner wall surface 31b is an obtuse angle (see FIG. 4). The boundary 31c is located between the first inner wall surface 31a and the second inner wall surface 31b.

The cover 30 prevents the liquid in the introduction chamber 13 from escaping through the opening 13a. Since the angle formed by the first inner wall surface 31a and second inner wall surface 31b is an obtuse angle, the liquid that comes in contact with the boundary 31c is unlikely to stay at the boundary 31c. Such a configuration can provide an effect of restricting reduction in the amount of the liquid that is to flow in the thermal convection pathway 11. Note that a configuration in which the boundary 31c is a curved face having an arc-like cross-section can provide substantially the same effect.

Figure 6:
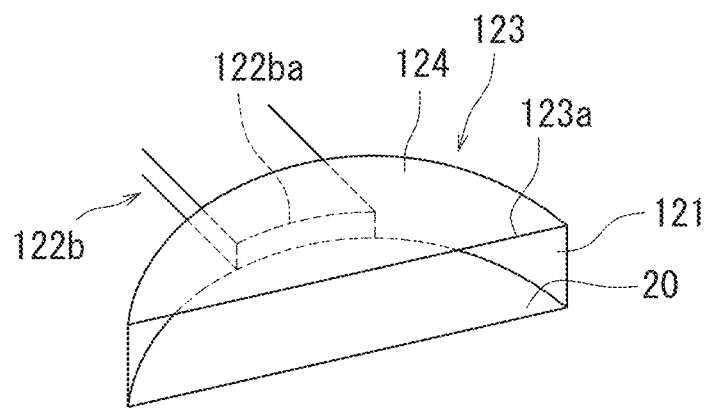
FIG. 6 is a diagram schematically illustrating a guide path of the thermal convection generating chip illustrated in FIG. 1.

A configuration of each guide passage 123 will be described in detail with reference to FIG. 6. FIG. 6 is a diagram schematically illustrating the guide passage 123.

Each guide passage 123 surrounds an entrance 122ba of the corresponding second region 122b. That is, a circular inner peripheral wall surface of the liquid receiving section 121, a substantially semicircular bottom wall surface of the guide passage forming section 124, and a top wall surface of the bottom plate 20 (see FIG. 1) form the guide passage 123. The guide passage 123 has a rectangular open face 123a. The open face 123a is located opposite to the entrance 122ba of the second region 122b. The open face 123a has an area larger than an aperture area of the entrance 122ba.

The liquid in the liquid receiving section 121 flows into the entrance 122ba while wetting wall surfaces around the entrance 122ba. Since the entrance 122ba is surrounded by three wall surfaces, the liquid readily flows into the entrance 122ba.

Since the open face 123a of the guide passage 123 has an area larger than the aperture area of the entrance 122ba, capillary action that causes the liquid to flow into the entrance 122ba is promoted compared to a configuration in which the open face 123a has an area smaller than or equal to the aperture area of the entrance 122ba. Thus, the liquid is facilitated to flow into the entrance 122ba.

In particular, provision of the guide passage 123 in the liquid receiving section 121 is effective in a configuration in which burr is formed at a periphery of the entrance 122ba. That is, the burr may block the liquid from flowing into the entrance 122ba, but provision of the guide passage 123 in the liquid receiving section 121 facilitates the liquid to flow into the entrance 122ba, reducing the adverse effect of the burr.

Note that the thermal convection generating chip 1 includes the plurality of thermal convection pathways 11 and the plurality of supply paths 12A to 12C, among which one set of supply paths 12A to 12C supplies liquids only to one thermal convection pathway 11. Each of the thermal convection pathways 11 is not in communication with the other thermal convection pathways 11. Accordingly, liquids are supplied to each of the thermal convection pathways 11 in an isolated manner.

The following describes a method for using the thermal convection generating chip 1 with reference to FIGS. 1 to 6.

First, a sample liquid is injected into the liquid receiving section 121 of a given one of the supply paths 12A. The amount of the sample liquid that is injected into the liquid receiving section 121 of the supply path 12A is greater than the amount of the sample liquid that fills the suction passage 122 of the supply path 12A, but does not need to be measured accurately.

After being injected, the sample liquid is caused to flow into the second region 122b of the suction passage 122 and further flow into the first region 122a by capillary action. Once the sample liquid reaches the one end portion 122aa of the first region 122a, the liquid flow caused by capillary action stops. As a result, the suction passage 122 is filled with the sample liquid over its entire length.

Likewise, a reactant solution is injected into the liquid receiving section 121 of the corresponding supply path 12B to fill the suction passage 122 of the supply path 12B with the reactant solution. Furthermore, mineral oil is injected into the liquid receiving section 121 of the corresponding supply path 12C to fill the suction passage 122 of the supply path 12C with the mineral oil.

Next, the chip main body 2 is attached to a drive shaft of a rotational drive mechanism of a thermal convection generating device (not illustrated) and driven to rotate about its central axis. As a result, centrifugal force is applied to the liquids in the suction passages 122 of the supply paths 12A to 12C. Consequently, the liquid in the first region 122a and the liquid in the second region 122b in each of the supply paths 12A to 12C move in directions to be separated from each other. That is, the liquid in the first region 122a flows into the introduction chamber 13, and the liquid in the second region 122b flows back to the liquid receiving section 121. It is preferable to provide a structure (for example, a liquid absorber) that prevents the liquid that has been back in the liquid receiving section 121 from escaping therefrom.

Of the liquids (the sample liquid, the reactant solution, and the mineral oil) that have flowed into the introduction chamber 13, the sample liquid and the reactant solution flow into the thermal convection pathway 11 through the introduction passage 15, whereas the mineral oil stays in the introduction passage 15. The sample liquid and the reactant solution in the thermal convection pathway 11 are heated by the heater. As a result, thermal convection is generated, and thus the sample liquid and the reactant solution are mixed together. Meanwhile, the mineral oil blocks the introduction passage 15 to restrict evaporation of the liquids in the thermal convection pathway 11 and back flow thereof into the introduction chamber 13.

As described above, the thermal convection generating chip 1 uses capillary action to fill the first regions 122a of the respective suction passages 122 with specified amounts of liquids and uses centrifugal force to cause the liquids to flow into the thermal convection pathway 11. Thus, a user can readily supply the specified amounts of liquids to the thermal convection pathway 11. It is therefore possible to reduce time and effort to be spent by the user in order to measure out the liquids.

Each of the thermal convection pathways 11 in the thermal convection generating chip 1 is not in communication with the other thermal convection pathways 11. Accordingly, thermal convection PCR can be performed on different types of liquids of different components at the same time.

Figure 7:
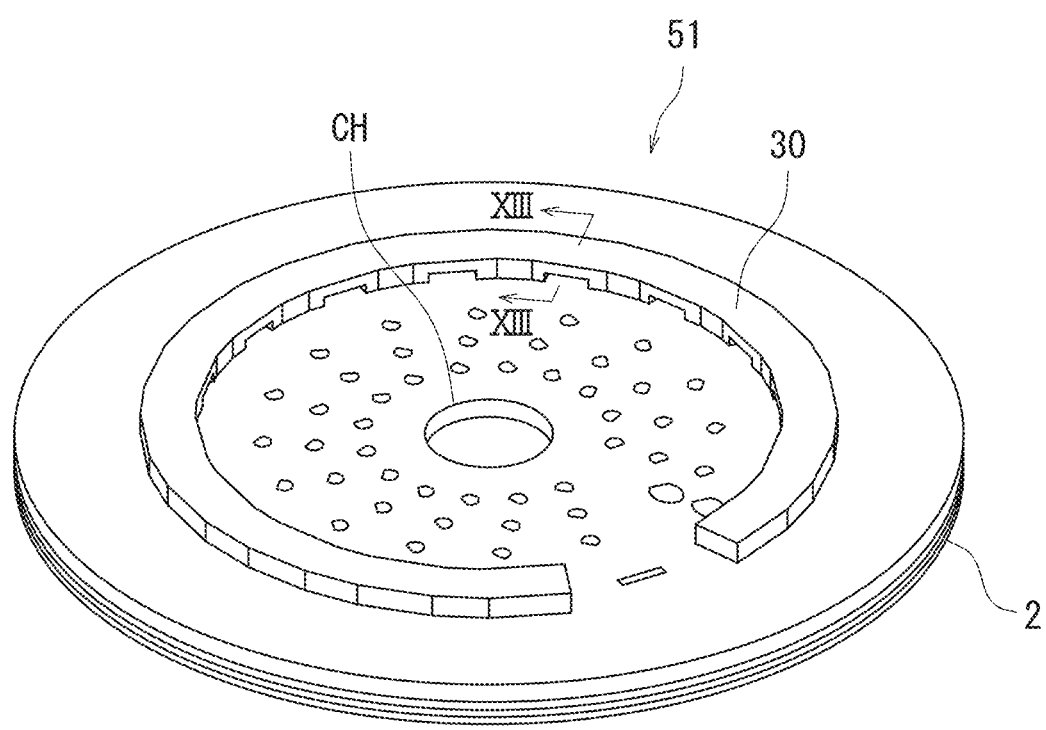
FIG. 7 is a perspective view of a thermal convection generating chip according to a second embodiment of the present invention.
Figure 8:
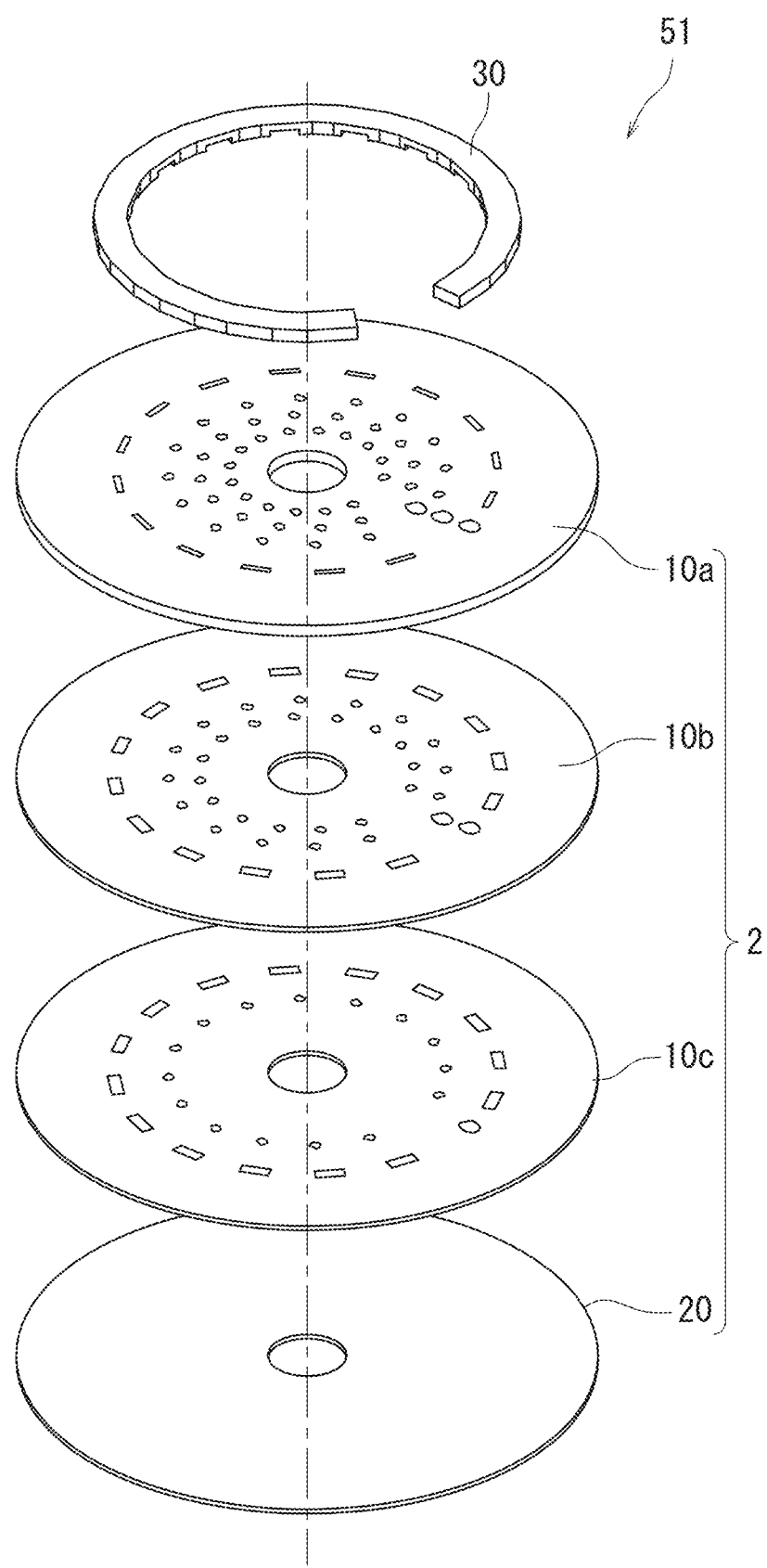
FIG. 8 is an exploded perspective view of the thermal convection generating chip illustrated in FIG. 7.

The following describes a second embodiment of the present invention. FIG. 7 is a perspective view of a thermal convection generating chip 51 according to the second embodiment of the present invention. FIG. 8 is an exploded perspective view of the thermal convection generating chip 51. Note that elements in the present embodiment that correspond to elements in the first embodiment are labelled using the same reference signs, and redundant description thereof that has been made for the first embodiment is omitted.

As illustrated in FIG. 7, a chip main body 2 of the thermal convection generating chip 51 has a multi-layer structure. That is, as illustrated in FIG. 8, the chip main body 2 includes a first substrate 10a, a second substrate 10b, a third substrate 10c, and a bottom plate 20. The first substrate 10a, the second substrate 10b, the third substrate 10c, and the bottom plate 20 are stacked on one another.

A structure of supply paths 12A to 12C of the thermal convection generating chip 51 will be described with reference to FIGS. 9A to 9D. FIGS. 9A to 9D are each a diagram schematically illustrating the structure of the supply paths 12A to 12C of the thermal convection generating chip 51.

Figure 9A:
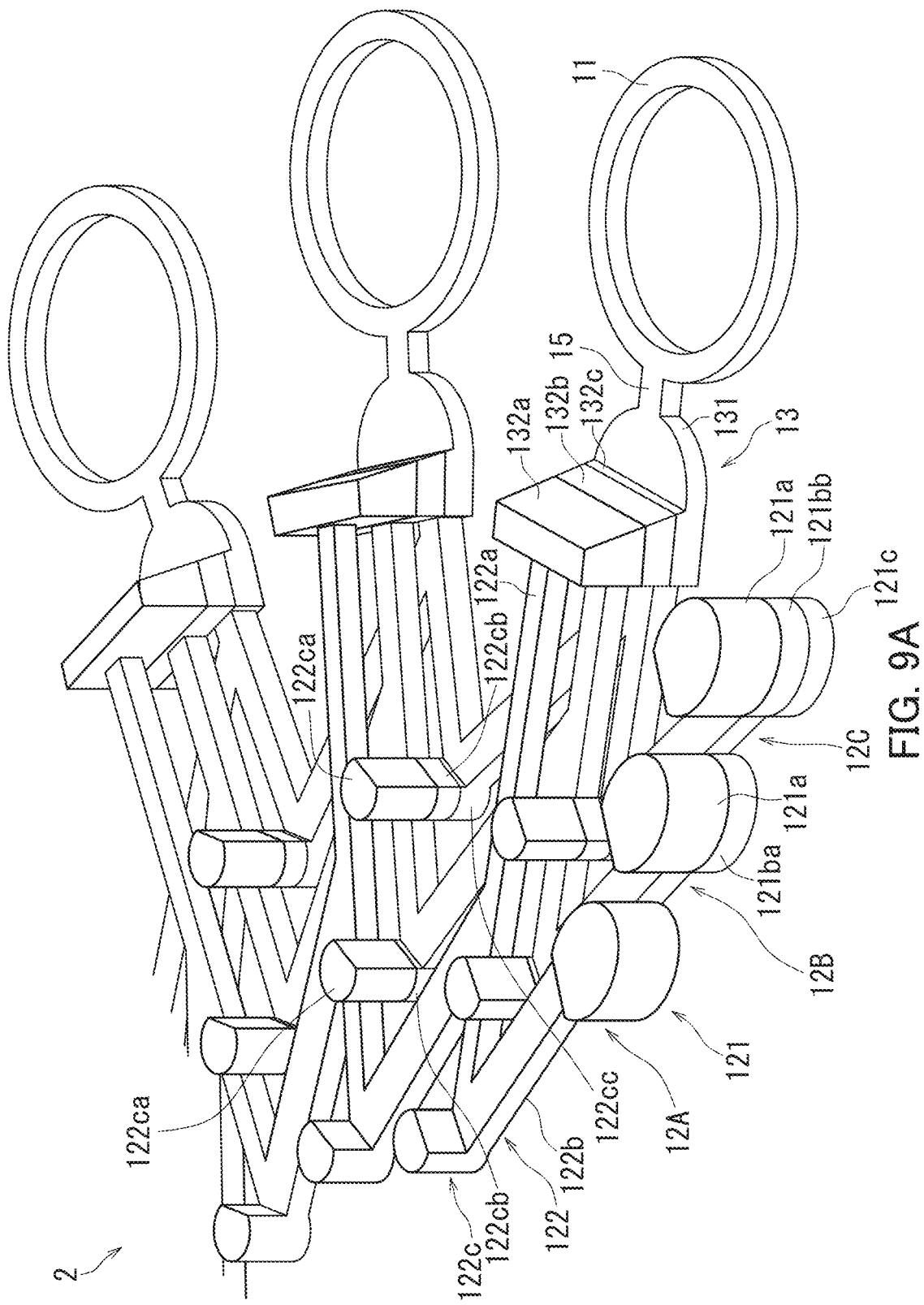
FIG. 9A is a diagram schematically illustrating a structure of supply paths of the thermal convection generating chip illustrated in FIG. 7.
Figure 9B:
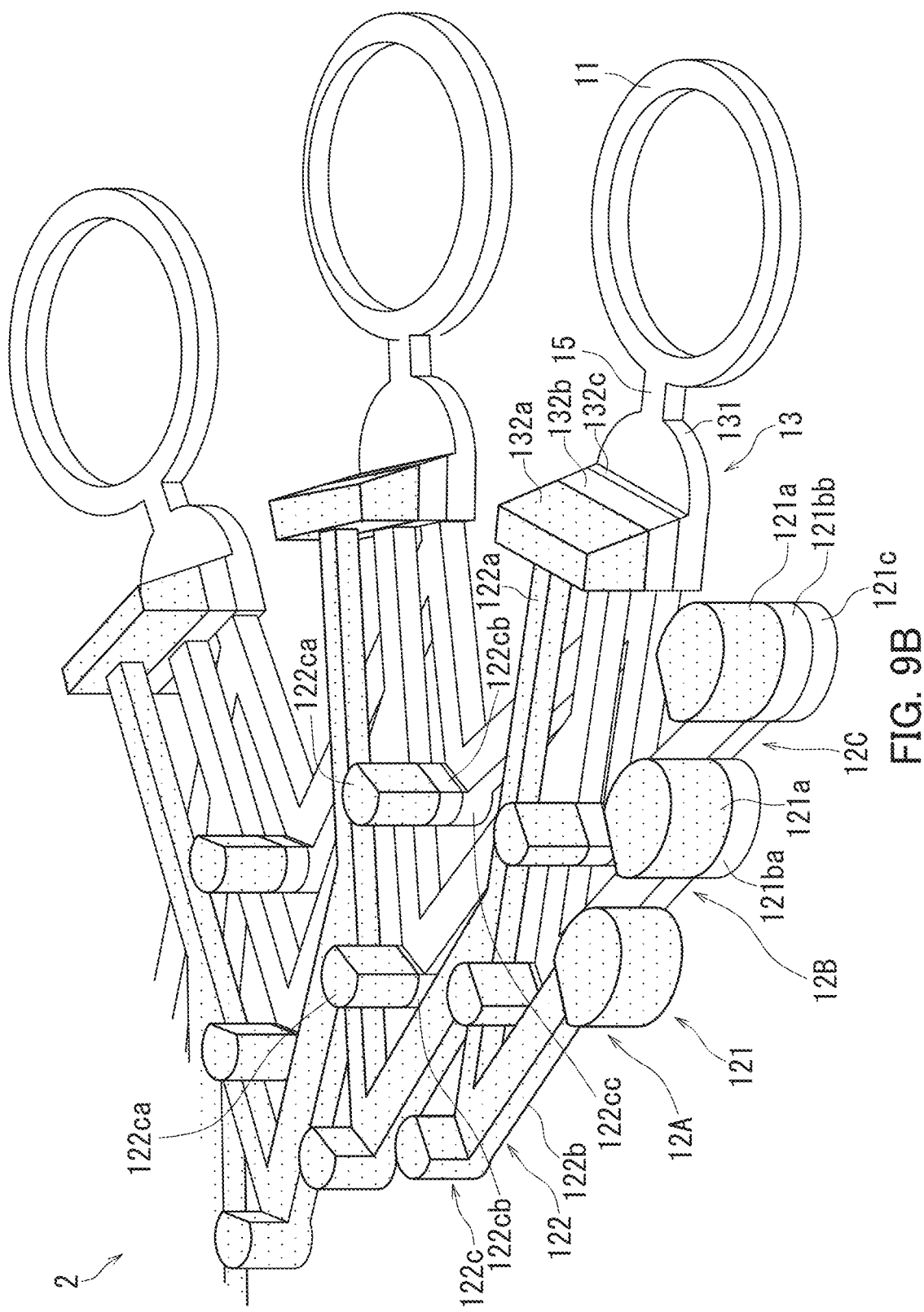
FIG. 9B is a diagram schematically illustrating the structure of the supply paths of the thermal convection generating chip illustrated in FIG. 7.
Figure 9C:
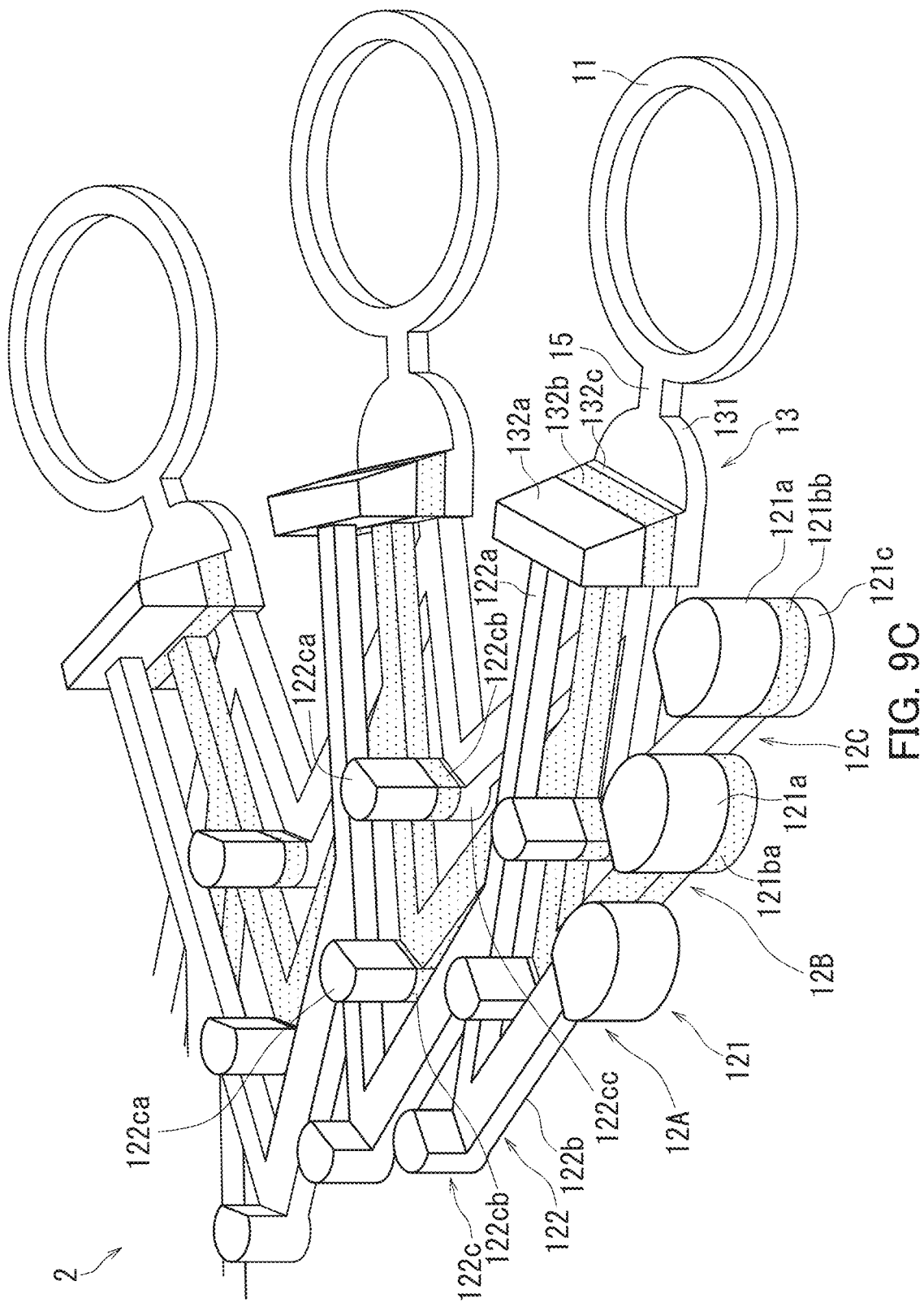
FIG. 9C is a diagram schematically illustrating the structure of the supply paths of the thermal convection generating chip illustrated in FIG. 7.
Figure 9D:
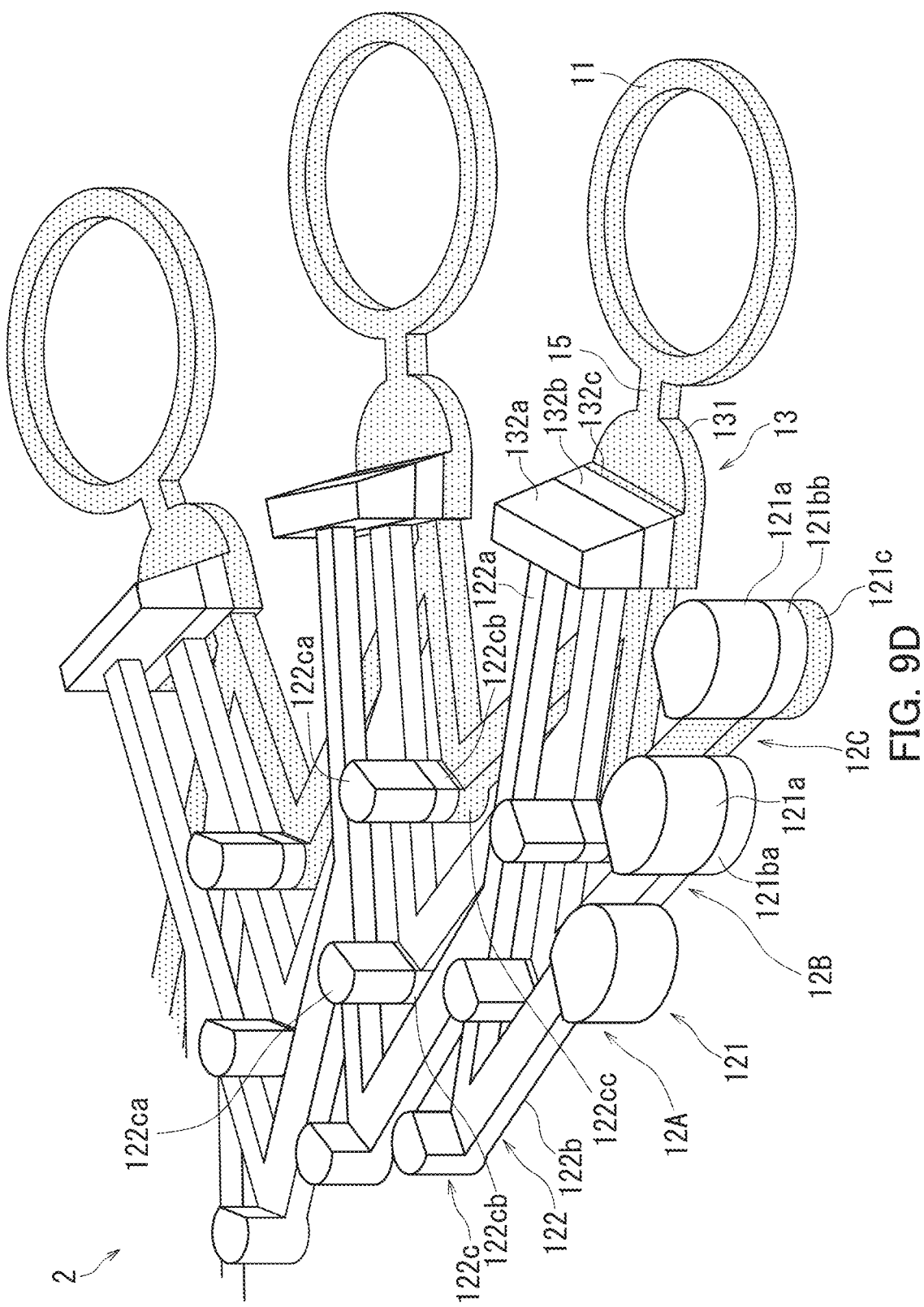
FIG. 9D is a diagram schematically illustrating the structure of the supply paths of the thermal convection generating chip illustrated in FIG. 7.

Note that in order to facilitate understanding, FIG. 9B distinguishes portions of the supply paths 12A to 12C that are formed in the first substrate 10a using shading. Likewise, FIG. 9C distinguishes portions of the supply paths 12A to 12C that are formed in the second substrate 10b using shading, and FIG. 9D distinguishes portions of the supply paths 12A to 12C that are formed in the third substrate 10c using shading.

The chip main body 2 includes a plurality of thermal convection pathways 11 and the supply paths 12A to 12C. Each of the supply paths 12A to 12C has one liquid receiving section 121 and a plurality of suction passages 122. Each of the thermal convection pathways 11 is provided with one of the suction passages 122 of each of the supply paths 12A to 12C between the thermal convection pathway 11 and the liquid receiving section 121 of each of the supply paths 12A to 12C. The supply paths 12A to 12C cross over one another at different levels, forming a labyrinth-like liquid passage.

As illustrated in FIGS. 8 and 9A to 9D, the supply path 12A is formed in the first substrate 10a. The supply path 12B is formed across the first substrate 10a and the second substrate 10b. The supply path 12C is formed across the first substrate 10a, the second substrate 10b, and the third substrate 10c.

The first substrate 10a has one liquid receiving section 121, a plurality of suction passages 122, a plurality of air inlets 122c, two holes 121a, a plurality of holes 122ca, and a plurality of holes 132a. One hole 121a of the two holes 121a forms a portion of the liquid receiving section 121 of the supply path 12B, and the other hole 121a forms a portion of the liquid receiving section 121 of the supply path 12C. Each of the suction passages 122 is provided with two holes 122ca. One hole 122ca of the two holes 122ca forms a portion of one air inlet 122c of the supply path 12B, and the other hole 122ca forms a portion of one air inlet 122c of the supply path 12C. Each of the suction passages 122 is provided with one hole 132a. The hole 132a forms a portion of one introduction chamber 13. Other than those described above, the configuration of the first substrate 10a will be described later with reference to FIG. 10.

The second substrate 10b has one hole 121ba, a plurality of suction passages 122, one hole 121bb, a plurality of holes 122cb, and a plurality of holes 132b. The hole 121ba and the hole 121a of the first substrate 10a form the liquid receiving section 121 of the supply path 12B. The hole 121bb forms a portion of the liquid receiving section 121 of the supply path 12C. Each of the suction passages 122 is provided with two holes 122cb. One hole 122cb of the two holes 122cb and one hole 122ca of the first substrate 10a form one air inlet 122c of the supply path B, and the other hole 122cb forms a portion of one air inlet 122c of the supply path 12C. Each of the suction passages 122 is provided with one hole 132b. The hole 132b forms a portion of one introduction chamber 13. Other than those described above, the configuration of the second substrate 10b will be described later with reference to FIG. 11.

The third substrate 10c has one hole 121c, a plurality of suction passages 122, a plurality of holes 122cc, a plurality of holes 132c, a plurality of grooves 131, and a plurality of introduction passages 15. The hole 121c, the hole 121bb of the second substrate 10b, and the other hole 121a of the first substrate 10a form the liquid receiving section 121 of the supply path 12C. Each of the suction passages 122 is provided with one hole 122cc. The hole 122cc, the other hole 122cb of the second substrate 10b, and the other hole 122ca of the first substrate 10a form one air inlet 122c of the supply path 12C. Each of the suction passages 122 is provided with one hole 132c. Each of the suction passages 122 is provided with one groove 131. The hole 132c and the groove 131 form a portion of one introduction chamber 13. Each of the suction passages 122 is provided with one introduction passage 15. Other than those described above, the configuration of the third substrate 10c will be described later with reference to FIG. 12.

Figure 10:
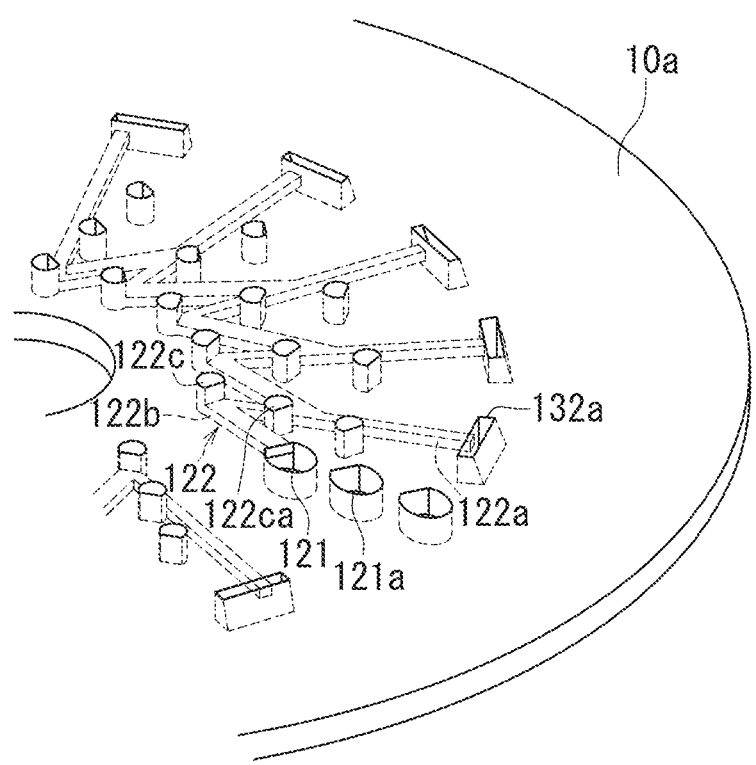
FIG. 10 is a partially enlarged, perspective view of a first substrate of the thermal convection generating chip illustrated in FIG. 7.

The configuration of the first substrate 10a will be described with reference to FIG. 10. FIG. 10 is a partially enlarged, perspective view of the first substrate 10a.

Each of the suction passages 122 has a first region 122a and a second region 122b. The first region 122a and the second region 122b each include a groove formed in a lower surface of the first substrate 10a. A midsection of the first region 122a of each suction passage 122 is connected with one end portion of the second region 122b of the adjacent suction passage 122. Thus, the plurality of suction passages 122 are in communication with one another.

Figure 11:
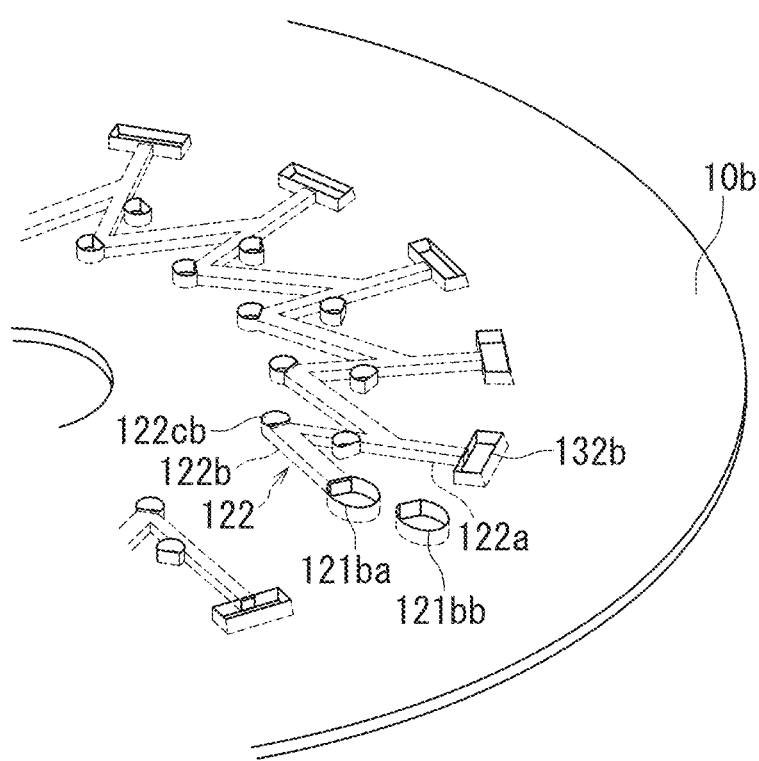
FIG. 11 is a partially enlarged, perspective view of a second substrate of the thermal convection generating chip illustrated in FIG. 7.

The following describes the configuration of the second substrate 10b with reference to FIG. 11. FIG. 11 is a partially enlarged, perspective view of the second substrate 10b.

Each of the suction passages 122 has a first region 122a and a second region 122b. The first region 122a and the second region 122b each include a groove formed in a lower surface of the second substrate 10b. A midsection of the first region 122a of each suction passage 122 is connected with one end portion of the second region 122b of the adjacent suction passage 122. Thus, the plurality of suction passages 122 are in communication with one another.

Figure 12:
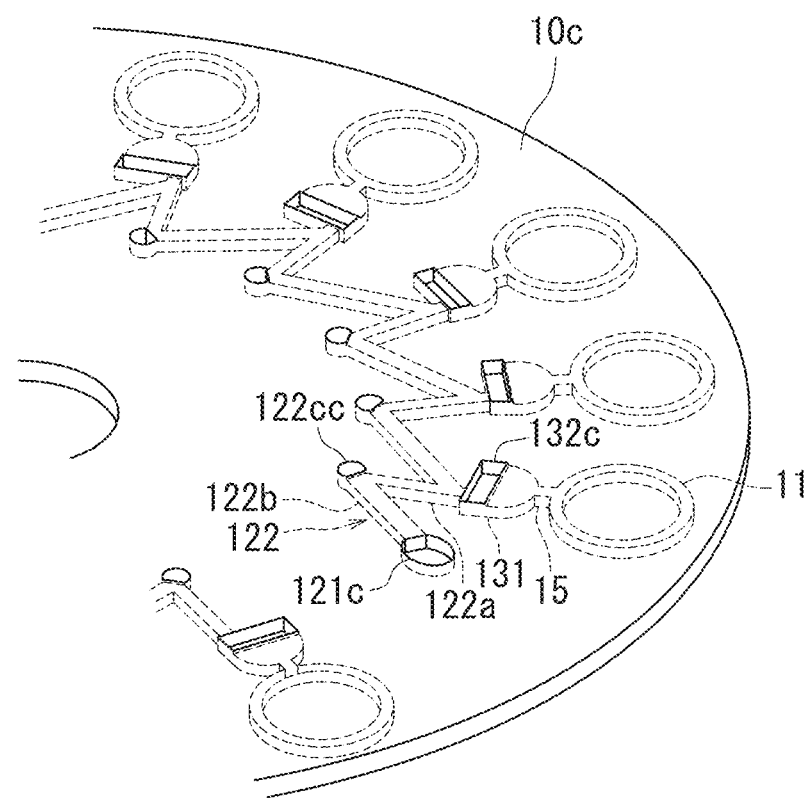
FIG. 12 is a partially enlarged, perspective view of a third substrate of the thermal convection generating chip illustrated in FIG. 7.

The following describes the configuration of the third substrate 10c with reference to FIG. 12. FIG. 12 is a partially enlarged, perspective view of the third substrate 10c.

The third substrate 10c has the plurality of thermal convection pathways 11. The thermal convection pathways 11 are arranged around a central axis of the third substrate 10c at predetermined angular spacing. Each of the suction passages 122 has a first region 122a and a second region 122b. The first region 122a and the second region 122b each include a groove formed in a lower surface of the third substrate 10c. A midsection of the first region 122a of each suction passage 122 is connected with one end portion of the second region 122b of the adjacent suction passage 122. Thus, the plurality of suction passages 122 are in communication with one another. Each groove 131 has a semi-oval shape in a plan view and is formed in the lower surface of the third substrate 10c. Each introduction passage 15 includes a groove formed in the lower surface of the third substrate 10c.

Figure 13:
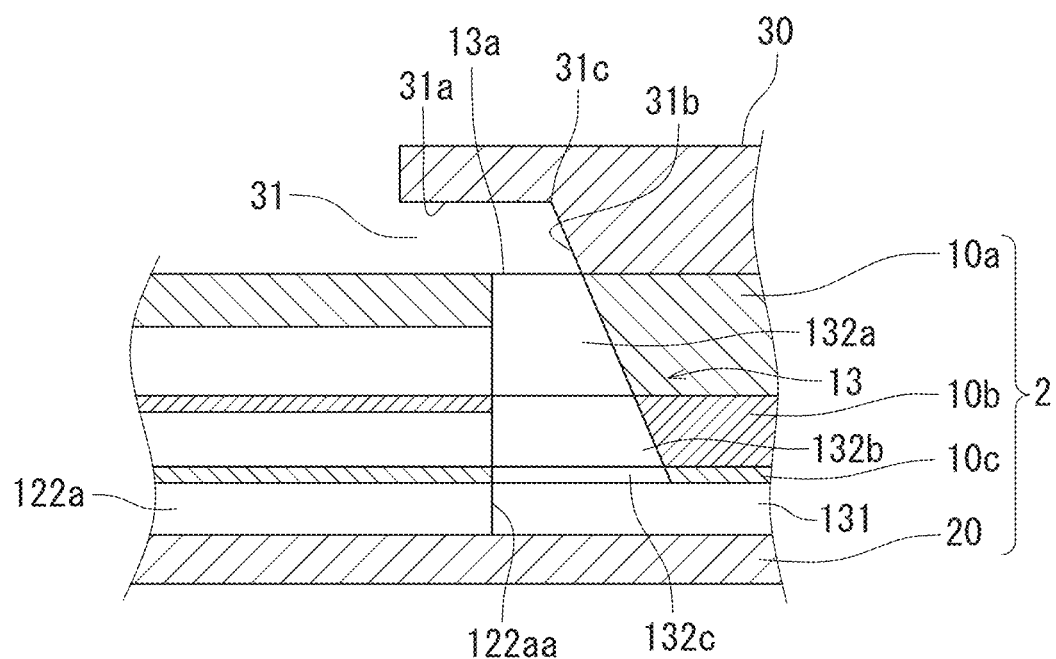
FIG. 13 is a cross-sectional view of the thermal convection generating chip taken along line XIII-XIII in FIG. 7.

The detailed configuration of the introduction chambers 13 will be described with reference to FIG. 13. FIG. 13 is a cross-sectional view taken along line VIII-VIII in FIG. 7. Each hole 132c has a trapezoidal vertical cross-section and is located above the corresponding groove 131. Each hole 132c is in communication with the corresponding groove 131 and the corresponding hole 132b. Each hole 132b is in communication with the corresponding hole 132a. Each hole 132a is in communication with a space outside the chip main body 2 through a corresponding one of openings 13a.

Figure 14:
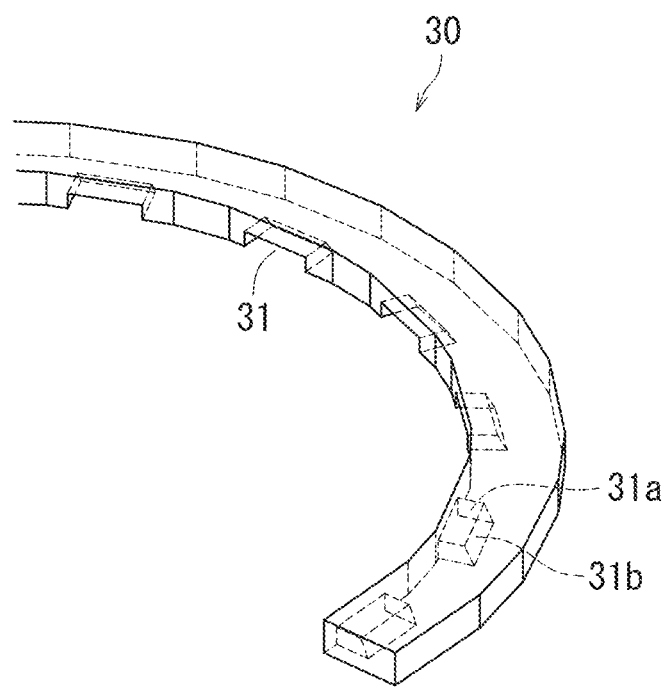
FIG. 14 is an enlarged perspective view of a cover of the thermal convection generating chip illustrated in FIG. 7.

The following describes a cover 30 with reference to FIG. 14. FIG. 14 is a perspective view of the cover 30. The cover 30 is a member having a C-shaped band-like shape in a plan view and has a plurality of recesses 31. The recesses 31 are arranged at predetermined intervals in a circumferential direction of the cover 30.

The following describes a method for using the thermal convection generating chip 51 with reference to FIGS. 7 to 14.

First, a sample liquid is injected into the liquid receiving section 121 of the supply path 12A. The amount of the sample liquid that is injected into the liquid receiving section 121 of the supply path 12A is greater than the amount of the sample liquid that fills all the suction passages 122 of the supply path 12A, but does not need to be measured accurately. After being injected into the liquid receiving section 121 of the supply path 12A, the sample liquid is caused to fill all the suction passages 122 of the supply path 12A by capillary action.

Likewise, a reactant solution is injected into the liquid receiving section 121 of the supply path 12B to fill all the suction passages 122 of the supply path 12B with the reactant solution. Furthermore, mineral oil is injected into the liquid receiving section 121 of the supply path 12C to fill all the suction passages 122 of the supply path 12C with the mineral oil.

Next, the chip main body 2 is attached to a drive shaft of a rotational drive mechanism of a thermal convection generating device (not illustrated) and driven to rotate about its central axis. As a result, centrifugal force is applied to the liquids in all the suction passages 122 of the respective supply paths 12A to 12C. Consequently, the liquid in the first region 122a and the liquid in the second region 122b in each of the suction passages 122 of the supply paths 12A to 12C move in directions to be separated from each other. That is, the liquid in each first region 122a flows into the corresponding introduction chamber 13, and the liquid in each second region 122b flows back to the corresponding liquid receiving section 121.

Of the liquids (the sample liquid, the reactant solution, and the mineral oil) that have flowed into the introduction chamber 13, the sample liquid and the reactant solution flow into the corresponding thermal convection pathway 11 through the corresponding introduction passage 15, whereas the mineral oil stays in the introduction passage 15. The sample liquid and the reactant solution in the thermal convection pathway 11 are heated by a heater. As a result, thermal convection is generated, and thus the sample liquid and the reactant solution are mixed together. Meanwhile, the mineral oil blocks the introduction passage 15 to restrict evaporation of the liquids in the thermal convection pathway 11, and back flow thereof into the introduction chamber 13.

As described above, the thermal convection generating chip 51 can supply a liquid to the plurality of thermal convection pathways 11 at the same time. For performing multiple runs of thermal convection PCR on a liquid of the same component at the same time, therefore, it is possible to reduce time and effort to be spent by a user in order to measure out the liquid.

Furthermore, since the supply paths 12A to 12C cross over one another at different levels in the thermal convection generating chip 51, the thermal convection generating chip 51 can be rendered compact in size.

Specific embodiments of the present invention have been described so far. However, the present invention is not limited to the embodiments. Note that the drawings of the embodiments are schematic illustrations that emphasize elements of configuration in order to facilitate understanding. Therefore, the illustrated elements of configuration may differ from the actual elements of configuration in order to aid preparation of the drawings. Also note that materials, shapes, and other properties described in the embodiments are only examples and are not intended to impose any particular limitations. Various alterations may be made so long as there in no substantial deviation from the effects of the present invention.

Figure 15:
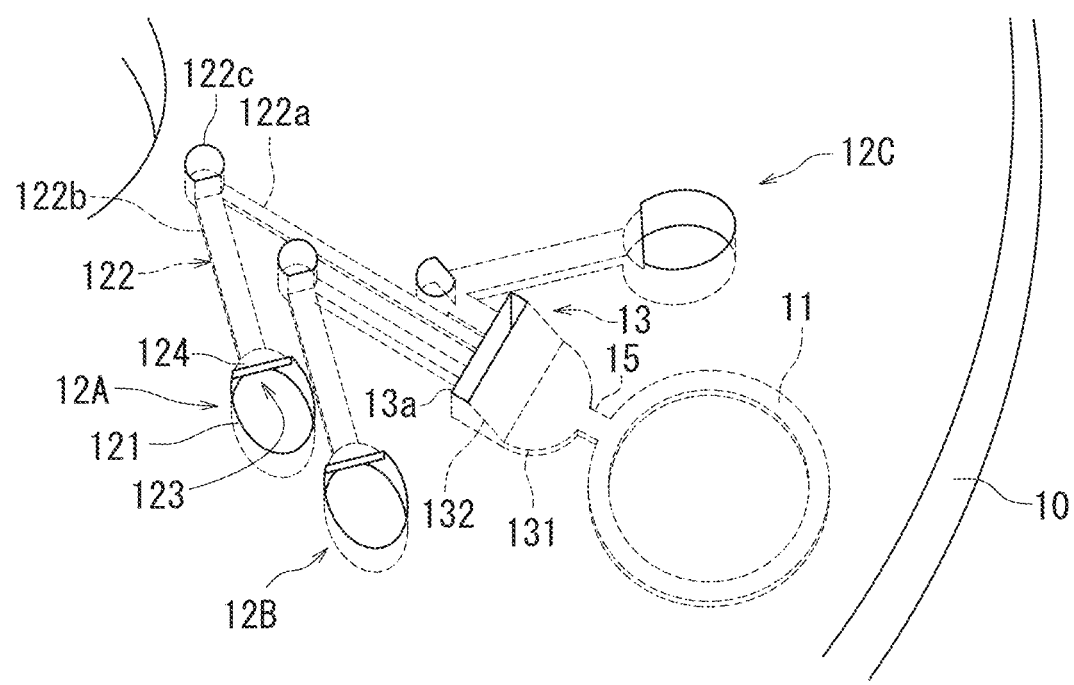
FIG. 15 is a partially enlarged, perspective view illustrating another configuration of the substrate of the thermal convection generating chip according to an embodiment of the present invention.

For example, the liquid receiving sections 121 of the three supply paths 12A to 12C are disposed at one side of one thermal convection pathway 11 in terms of a circumferential direction of the chip main body 2 in the thermal convection generating chips according to the first and second embodiments. Alternatively, the three liquid receiving sections 121 may be distributed at opposite sides of the thermal convection pathway 11. FIG. 15 is a partially enlarged, perspective view illustrating another configuration of the substrate 10 of the thermal convection generating chip 1. As illustrated in FIG. 15, for example, the liquid receiving sections 121 of the supply paths 12A and 12B may be disposed at one side of the thermal convection pathway 11, and the liquid receiving section 121 of the supply path 12C may be disposed at the other side of the thermal convection pathway 11.

The thermal convection generating chips according to the first and second embodiments each include a plurality of thermal convection pathways. Alternatively, the present invention is applicable to a thermal convection generating chip having one thermal convection pathway.

Each thermal convection pathway is provided with three supply paths in the thermal convection generating chips according to the first and second embodiments. Alternatively, each thermal convection pathway may be provided with two or fewer supply paths or four or more supply paths.

The rotatory body includes one or three substrates in the first and second embodiments. Alternatively, the rotatory body may include two substrates or four or more substrates.

Each thermal convection pathway is provided with one supply path for supplying a reactant solution to the thermal convection pathway in the first and second embodiments. Alternatively, each thermal convection pathway may be provided with a plurality of supply paths for supplying reactant solutions to the thermal convection pathway, and the plurality of supply paths may be configured to supply reactant solutions to the thermal convection pathway. Such a configuration allows different types of reactant solutions to be supplied to one thermal convection pathway at the same time.

The thermal convection generating chips according to the first and second embodiments include a supply path for supplying a sample liquid to a thermal convection pathway, a supply path for supplying a reactant solution to the thermal convection pathway, and a supply path for supplying an evaporation inhibitor liquid to the thermal convection pathway. Alternatively, the thermal convection generating chips may include only one or two of the three different supply paths.

According to the first and second embodiments, the supply path 12A supplies a sample liquid to the thermal convection pathway 11, the supply path 12B supplies a reactant solution to the thermal convection pathway 11, and the supply path 12C supplies an evaporation inhibitor liquid to the thermal convection pathway 11. However, what is supplied by the respective supply paths 12A to 12C can be determined as appropriate. For example, it may be determined that the supply path 12A supplies a reactant solution to the thermal convection pathway 11 and the supply path 12B supplies a sample liquid to the thermal convection pathway 11.

According to the first and second embodiments, the total volume of the volumes of two first regions in communication with a thermal convection pathway is equal to the volume of the thermal convection pathway. Alternatively, the total volume of the volumes of three or more first regions in communication with a thermal convection pathway may be equal to the volume of the thermal convection pathway. Alternatively, the volume of one first region in communication with a thermal convection pathway may be equal to the volume of the thermal convection pathway.

The present invention can also provide a liquid measuring device for measuring out not only a liquid to be subjected to thermal convection but also any other liquids. The liquid measuring device includes, of the elements of configuration of the thermal convection generating chip 1 illustrated in FIGS. 1 to 3A, 3B, and 15, at least a rotatory body (chip main body) 2, a liquid receiving section 121, and a suction passage 122. The liquid measuring device measures out a specified amount of liquid. The liquid measuring device includes the rotatory body 2, the liquid receiving section 121 provided in the rotatory body 2, and the suction passage 122 that is in communication with the liquid receiving section 121 and sucks a liquid in the liquid receiving section 121 by capillary action. The suction passage 122 has a first region 122a extending between a midsection of the suction passage 122 and an end of the suction passage 122, and a second region 122b extending between the midsection of the suction passage 122 and the liquid receiving section 121. The liquid in the first region 122a is separated from the liquid in the second region 122b through rotation of the rotatory body 2 to be discharged from the end of the suction passage 122.

Other than those describe above, various alterations may be made to the embodiments so long as there is no substantial deviation from the effects of the present invention.

Examples

The following describes an example of the present invention. However, the present invention is not limited to the following example.

In the present example, detection of Methicillin resistant *Staphylococcus aureus* (MRSA) genomic DNA was carried out using the thermal convection generating chip 1. More specifically, DNA of the mecA region of the MRSA genome was amplified by PCR.

Figure 16:
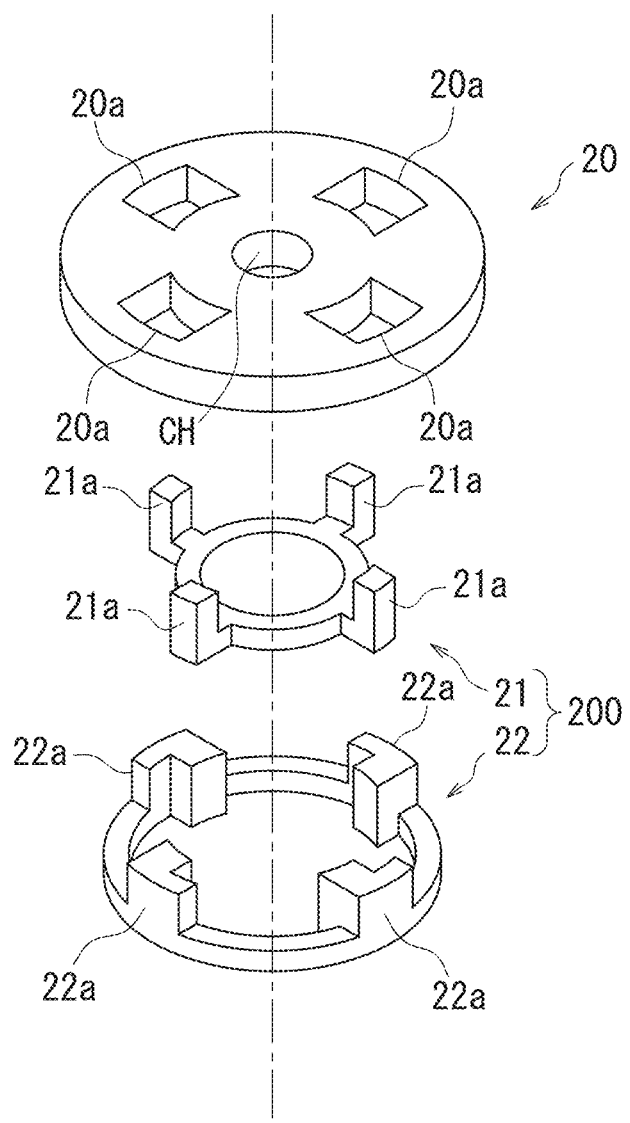
FIG. 16 is an exploded perspective view illustrating a ring-shaped heater used in an example of the present invention.
Figure 17:
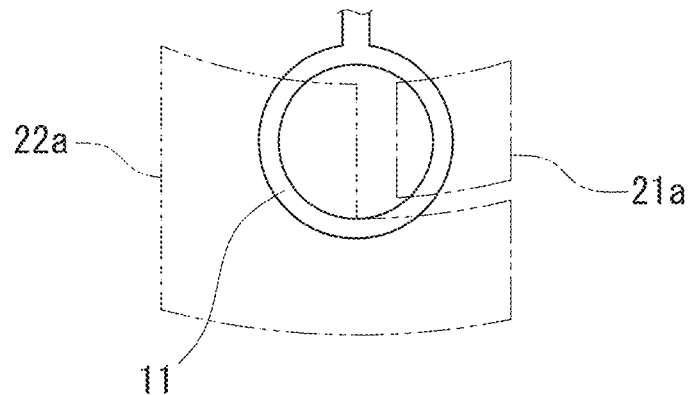
FIG. 17 is a plan view illustrating a positional relationship between a thermal convection pathway and the ring-shaped heater in the example of the present invention.

In the present example, the thermal convection generating chip 1 having a ring-shaped heater was used. FIG. 16 is an exploded perspective view illustrating the ring-shaped heater used in the present example. FIG. 17 is a plan view illustrating a positional relationship between one thermal convection pathway 11 and the ring-shaped heater in the present example.

As illustrated in FIG. 16, a ring-shaped heater 200 included a first ring-shaped heater 21 and a second ring-shaped heater 22. The first ring-shaped heater 21 included four first protrusions 21a, and the second ring-shaped heater 22 included four second protrusions 22a. Four through holes 20a were formed in the bottom plate 20. The four first protrusions 21a were inserted into the through holes 20a in one-to-one correspondence, and the four second protrusions 22a were inserted into the through holes 20a in one-to-one correspondence. Furthermore, the substrate 10 of the thermal convection generating chip 1 was provided with the thermal convection pathways 11 in positions corresponding to the respective through holes 20a. That is, as illustrated in FIG. 17, the substrate 10 was placed on the bottom plate 20 such that each of the thermal convection pathways 11 was disposed opposite to one set of the first protrusion 21a and the second protrusion 22a (one through hole 20a of the bottom plate 20). In the present example, the first ring-shaped heater 21 (first protrusions 21a) was heated to 95° C., and the second ring-shaped heater 22 (second protrusions 22a) was heated to 60° C.

Furthermore, a shaft of a DC motor was fixed in the center hole CH of the chip main body 2, and the DC motor was used to rotate the chip main body 2. The rotational speed of the chip main body 2 was controlled by adjusting voltage that was supplied to the DC motor.

The material of the chip main body 2 (the substrate 10 and the bottom plate 20) was a cyclic olefin. Channels (thermal convection pathways 11 and supply paths 12A to 12C) were formed in the cyclic olefin substrate 10 by cutting the substrate 10. The thermal convection pathway 11 had a channel width of 500 μm and a depth of 400 μm. Furthermore, inner wall surfaces of the channels formed in the substrate 10 were coated with a surfactant. An aqueous solution of polyoxyethylene sorbitan monolaurate was used as the surfactant. More specifically, an aqueous solution containing 1 wt % of TWEEN (registered trademark) 20 produced by Sigma-Aldrich was used.

In the present example, a MRSA genomic DNA solution (sample liquid) having a concentration of 20 ng/μL was added dropwise into the liquid receiving section 121 of the supply path 12B, a PCR reaction solution containing primer DNA and probe DNA (reactant solution) was added dropwise into the liquid receiving section 121 of the supply path 12A, and mineral oil (evaporation inhibitor liquid) was added dropwise into the liquid receiving section 121 of the supply path 12C. Table 1 shows base sequences of the primer DNA and the probe DNA (MRSA genomic DNA, mecA) that were used in the present example. Table 2 shows a composition of the PCR reaction solution.

| Primer and Probe | Sequences (5'→3') | Amplified length |
|---|---|---|
| Forward primer | GGCAATATTACCGCACCTCA | 214 bp |
| Reverse primer | GTCTGCCACTTTCTCCTTGT | |
| TaqMan probe | AGATCTTATGCAAACTTAAT TGGCAAATCC | |

TABLE 2

| PCR solution contents | Final concentration |
|---|---|
| 2× Ampdirect ® Plus (product of Shimadzu Corporation) | 1× |
| SpeedSTAR ™ HS DNA Polymerase 5 U/μL (product of TAKARA BIO INC.) | 0.25 U/μL |
| Forward primer | 300 nM |
| Reverse primer | 300 nM |
| Probe (FAM(5')-TAMRA ™(3')) | 300 nM |
| Bovine serum albumin (product of Sigma-Aldrich) | 0.1% (w/v) |
| Polyvinylpyrrolidone (product of Sigma-Aldrich) | 0.01% (v/v) |
| D.W. | |

After the MRSA genomic DNA solution had filled the first region 122a of the supply path 12B through capillary action, the PCR reaction solution had filled the first region 122a of the supply path 12A through capillary action, and the mineral oil had filled the first region 122a of the supply path 12C through capillary action, the chip main body 2 was driven to rotate at a rotational speed of 3,270 rpm to introduce the MRSA genomic DNA solution and the PCR reaction solution into the thermal convection pathway 11. Subsequently, the temperature of the ring-shaped heater 200 was adjusted, and the chip main body 2 was driven to rotate such that the chip main body 2 was subjected to 5G of relative gravitational acceleration. The MRSA genomic DNA solution and the PCR reaction solution were reacted for 15 minutes.

Figure 18:
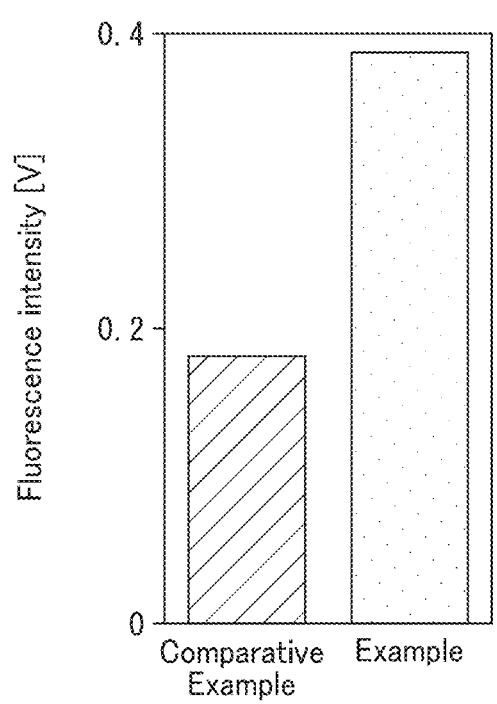
FIG. 18 is a diagram showing a measurement result of the example of the present invention.

After a PCR reaction was detected (after 15 minutes had elapsed), a fluorescence intensity of the solution contained in the thermal convection pathway 11 was measured. FIG. 18 shows the measurement result. As a comparative example, a sample liquid containing no MRSA genomic DNA was used to carry out the PCR reaction detection in the same manner as in the present example, and the fluorescence intensity was measured. FIG. 18 also shows the measurement result of the comparative example.

The vertical axis in FIG. 18 represents fluorescence intensity. As shown in FIG. 18, the experiment (example) in which the sample liquid contained MRSA genomic DNA resulted in a greater fluorescence intensity than the experiment (comparative example) in which the sample liquid contained no MRSA genomic DNA.

Figure 19A:
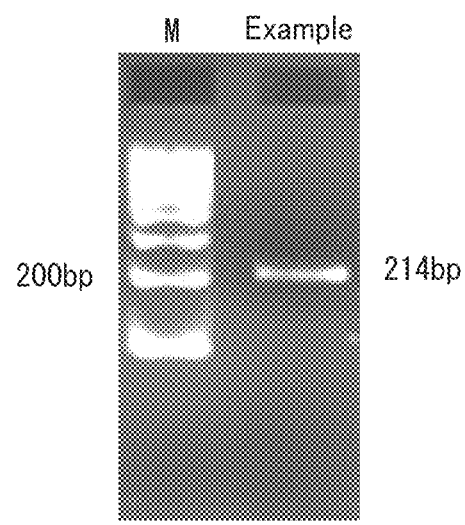
FIG. 19A is a photograph showing an analysis result of the example of the present invention.
Figure 19B:
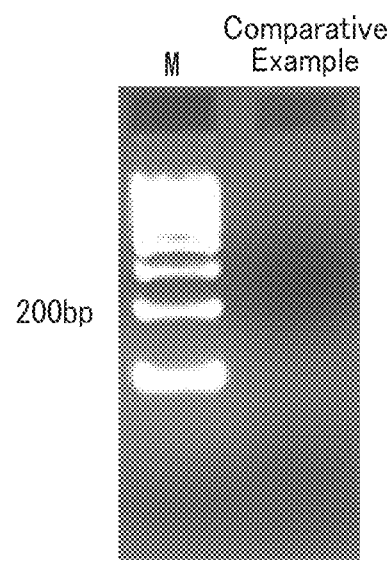
FIG. 19B is a photograph showing an analysis result of a comparative example.

Furthermore, electrophoresis was performed to analyze amplified products. FIGS. 19A and 19B show the analysis results. FIG. 19A is a photograph showing the analysis result of the amplified product of the present example. FIG. 19B is a photograph showing the analysis result of the amplified product of the comparative example. The letter M in FIGS.

19A and 19B represents DNA size markers. As shown in FIGS. 19A and 19B, a DNA band (214 bp) of the mecA gene, which was a detection target, was observed only in the experiment (example) in which the sample liquid contained MRSA genomic DNA.

As proved above, the thermal convection generating chip 1 enabled sorting, aliquoting, and mixing of solutions, which are necessary for PCR. Furthermore, the thermal convection generating chip 1 enabled a DNA amplification reaction.

REFERENCE SIGNS LIST

1 Thermal convection generating chip
2 Chip main body (rotatory body)
10 Substrate
10a First substrate
10b Second substrate
10c Third substrate
11 Thermal convection pathway
12A, 12B, 12C Supply path
121 Liquid receiving section
122 Suction passage
122a First region
122b Second region
122ba Entrance
122c Air inlet
123 Guide passage
123a Open face
13 Introduction chamber
13a Opening
30 Cover
31 Recess
31a First inner wall surface
31b Second inner wall surface

The invention claimed is:

1. A thermal convection generating chip for generating thermal convection of at least one liquid, comprising:
a rotatory body having a central axis, an outer circumferential edge, and an upper surface, the rotatory body being configured to rotate about the central axis;
a thermal convection pathway provided in the rotatory body;
a first supply path configured to supply one of the at least one liquid to the thermal convection pathway;
a second supply path configured to supply another of the at least one liquid to the thermal convection pathway;
an introduction chamber disposed between the first region of the suction passage and the thermal convection pathway; and
a cover disposed on the upper surface of the rotatory body and protruding from the upper surface of the rotatory body,
the thermal convection pathway being an annular groove located inside the rotatory body and being configured to generate thermal convection of the liquid supplied from the first supply path and the liquid supplied from the second supply path,
the first supply path and the second supply path each including:
a liquid receiving section configured to receive the liquid, the liquid receiving section being a first hole in the rotatory body, the first hole having an opening in the upper surface of the rotatory body; and
a suction passage configured to provide communication between the liquid receiving section and the thermal convection pathway, and suck the liquid in the liquid receiving section by capillary action to fill the suction passage with the liquid over an entire length thereof, the suction passage being a groove located inside the rotatory body, wherein
the suction passage has a midsection, a first region, a second region, and an air inlet, and bends at the midsection,
the first region extends between the midsection and the thermal convection pathway in a radial direction from the midsection toward the outer circumferential edge of the rotatory body,
the second region extends between the midsection and the liquid receiving section in a direction that is from the midsection toward the outer circumferential edge of the rotatory body and that intersects with the radial direction in which the first region extends,
an angle between the first region and the second region is less than 90°, so that the liquid in the first region and the liquid in the second region move in directions to be separated from each other through rotation of the rotatory body, and thus the liquid in the first region is supplied to the thermal convection pathway,
the air inlet is a hole in the upper surface of the rotatory body,
the air inlet is located opposite to the midsection in an extending direction of the central axis of the rotatory body and configured to provide communication between an outer space at the upper surface of the rotatory body and the midsection to allow air to be introduced into the midsection through the air inlet,
the introduction chamber includes a groove located inside the rotatory body and a second hole provided adjacent to the upper surface of the rotatory body,
the second hole is located above the groove and is in communication with the groove of the introduction chamber,
the second hole has an opening in the upper surface of the rotatory body,
the introduction chamber is connected with an end portion of the first region toward the thermal convection pathway and is in communication with the outer space through the second hole, and
the cover covers the second hole.

2. The thermal convection generating chip according to claim 1, wherein
the first supply path or the second supply path supplies a sample liquid containing DNA or RNA to the thermal convection pathway.

3. The thermal convection generating chip according to claim 1, wherein
the first supply path or the second supply path supplies a reactant solution for PCR or reverse transcription-PCR to the thermal convection pathway.

4. The thermal convection generating chip according to claim 1, comprising
a plurality of the first supply paths or a plurality of the second supply paths, wherein
the first supply paths or the second supply paths each supply a reactant solution for PCR or reverse transcription-PCR to the thermal convection pathway.

5. The thermal convection generating chip according to claim 1, further comprising:
an introduction passage disposed between the introduction chamber and the thermal convection pathway; and
a third supply path configured to supply an evaporation inhibitor liquid to the introduction passage through the introduction chamber, the evaporation inhibitor liquid inhibiting evaporation of the liquid in the thermal convection pathway, wherein
the introduction chamber provides communication between an end portion of the first region toward the thermal convection pathway and the introduction passage, and
the introduction passage includes a groove located inside the rotatory body and provides communication between the introduction chamber and the thermal convection pathway.

6. The thermal convection generating chip according to claim 1, wherein
one of the first supply path and the second supply path supplies a sample liquid containing DNA or RNA to the thermal convection pathway,
the other of the first supply path and the second supply path supplies a reactant solution for PCR or reverse transcription-PCR to the thermal convection pathway, and
a total volume of a volume of the first region of the first supply path and a volume of the first region of the second supply path is equal to a volume of the thermal convection pathway.

7. The thermal convection generating chip according to claim 1, wherein
the cover has a recess in communication with the outer space and with the introduction chamber,
the recess has a first inner wall surface located opposite to the second hole and a second inner wall surface intersecting with the first inner wall surface, and
an angle formed by the first inner wall surface and the second inner wall surface is an obtuse angle, or a boundary between the first inner wall surface and the second inner wall surface is a curved face having an arc-like cross-section.

8. The thermal convection generating chip according to claim 1, wherein
the first supply path and the second supply path each further include a guide passage configured to guide the liquid in the liquid receiving section to the second region,
the guide passage surrounds an entrance of the second region and has an open face located opposite to the entrance, and
the open face of the guide passage has an area larger than an aperture area of the entrance.

9. The thermal convection generating chip according to claim 8, wherein
the open face of the guide passage is rectangular.

10. The thermal convection generating chip according to claim 8, further comprising
a guide passage forming section covering a portion of a top face of the liquid receiving section, the portion being located toward the entrance of the second region, wherein
the guide passage is located between the guide passage forming section and the liquid receiving section.

11. The thermal convection generating chip according to claim 10, wherein
the rotatory body has a substrate and a bottom plate laminated to the substrate,
the liquid receiving section is located in the substrate,
an inner peripheral wall surface of the liquid receiving section, a bottom wall surface of the guide passage forming section, and a top wall surface of the bottom plate form the guide passage.

12. The thermal convection generating chip according to claim 1, comprising
a plurality of the thermal convection pathways.

13. The thermal convection generating chip according to claim 1, comprising
a plurality of the thermal convection pathways, wherein
the first supply path and the second supply path each include the liquid receiving section and a plurality of the suction passages,
each of the thermal convection pathways is provided with one of the suction passages of the first supply path between the thermal convection pathway and the liquid receiving section of the first supply path, and
each of the thermal convection pathways is provided with one of the suction passages of the second supply path between the thermal convection pathway and the liquid receiving section of the second supply path.

14. The thermal convection generating chip according to claim 13, wherein the suction passages of the first supply path and the suction passages of the second supply path cross over one another at different levels.

15. The thermal convection generating chip according to claim 14, wherein
the rotatory body has a first substrate and a second substrate stacked on one another,
the liquid receiving section of one of the first supply path and the second supply path is located in one of the first substrate and the second substrate, and
the liquid receiving section of the other of the first supply path and the second supply path is located across the first substrate and the second substrate.

16. The thermal convection generating chip according to claim 1, wherein
a total volume of a volume of the first region of the first supply path and a volume of the first region of the second supply path is equal to a volume of the thermal convection pathway.

17. The thermal convection generating chip according to claim 1, wherein
the second hole has a trapezoidal cross-section.

* * * * *